(12) United States Patent
Nam et al.

(10) Patent No.: US 11,278,579 B2
(45) Date of Patent: Mar. 22, 2022

(54) ***LACTOBACILLUS PARACASEI* AO356 STRAIN HAVING ANTI-OBESITY ACTIVITY AND METHOD FOR PREVENTING, ALLEVIATING OR TREATING OBESITY USING THE SAME**

(71) Applicant: KOREA FOOD RESEARCH INSTITUTE, Jeollabuk-do (KR)

(72) Inventors: Young Do Nam, Seongnam-si (KR); So Young Lee, Yongin-si (KR); Hee Soon Shin, Gyeonggi-do (KR); So Lim Park, Busan (KR); Won Hyong Chung, Daegu (KR); Eun Sook Lee, Seoul (KR); Eun Ji Song, Busan (KR); Dong Uk Shin, Cheongju-si (KR)

(73) Assignee: KOREA FOOD RESEARCH INSTITUTE, Wanju-Gun (KR)

( * ) Notice: Subject to any disclaimer, the term of this patent is extended or adjusted under 35 U.S.C. 154(b) by 0 days.

(21) Appl. No.: 16/903,955

(22) Filed: Jun. 17, 2020

(65) Prior Publication Data

US 2021/0393706 A1    Dec. 23, 2021

(51) Int. Cl.
| | | |
|---|---|---|
| *A61K 35/747* | (2015.01) | |
| *A61K 39/09* | (2006.01) | |
| *A61K 35/00* | (2006.01) | |
| *A61K 35/742* | (2015.01) | |
| *C12R 1/225* | (2006.01) | |

(52) U.S. Cl.
CPC .......... *A61K 35/742* (2013.01); *A61K 35/747* (2013.01); *A61K 39/09* (2013.01); *A61K 2035/115* (2013.01); *C12R 2001/225* (2021.05)

(58) Field of Classification Search
None
See application file for complete search history.

(56) References Cited

U.S. PATENT DOCUMENTS

2020/0270709 A1*   8/2020   Park .................. A61K 35/742

FOREIGN PATENT DOCUMENTS

KR   10-2019-0068078 A   6/2019

OTHER PUBLICATIONS

Sayej et al. BioMed Research International, vol. 2016, article #7867852, pp. 1-12, 2016.*

* cited by examiner

*Primary Examiner* — Sarvamangala Devi
(74) *Attorney, Agent, or Firm* — Sughrue Mion, PLLC

(57) ABSTRACT

A novel *Lactobacillus paracasei* AO356 strain according to the present disclosure, which is a strain isolated from the human body, has high stability, exhibits the activity of inhibiting adipogenic differentiation in vitro and inducing the differentiation of M1 and M0 macrophages into M2 macrophages, and has excellent activity of alleviating, preventing, or treating obesity, such as the activity of reducing body weight and a reduction in blood lipid concentration through the browning of white fat in animal experiments. Thus, the novel strain of the present disclosure has a low possibility of causing side effects, and therefore, unlike conventional diet functional foods or drugs, which have side effect problems, a diet effect can be exhibited without controlling the dose thereof. Accordingly, the novel strain can be used as a pharmaceutical composition for treating or preventing obesity or a food composition for alleviating or preventing obesity.

6 Claims, 24 Drawing Sheets
Specification includes a Sequence Listing.

LACTOBACILLUS PARACASEI AO356 STRAIN HAVING ANTI-OBESITY ACTIVITY AND METHOD FOR PREVENTING, ALLEVIATING OR TREATING OBESITY USING THE SAME

BACKGROUND

1. Field

The present disclosure relates to a novel *Lactobacillus paracasei* AO356 strain having anti-obesity activity, and a method for preventing, alleviating or treating obesity using the same.

2. Discussion of Related Art

As mankind has developed into a rich society, obesity has emerged as one of the most serious chronic diseases. Obesity occurs due to various causes, is a metabolic disorder caused by an imbalance between intake and consumption of calories, and morphologically, is known to be caused by hypertrophy or hyperplasia of adipocytes in the body.

Obesity has become a direct cause that not only psychologically disturbs individuals, but also increases the risk of various adult diseases socially, and thus is a major cause of an increase in national medical spending.

Specifically, obesity is directly associated with the increased prevalence of various adult diseases such as type 2 diabetes, hypertension, hyperlipidemia, and cardiovascular disease, and all obesity-related diseases are referred to as metabolic syndrome or insulin resistance syndrome. These act as causes of arteriosclerosis and cardiovascular diseases.

Obesity is not only the most common malnutrition disorder in western society, but also in Korea, the frequency of obesity tends to be rapidly increasing due to the improvement of diet and westernization of lifestyles, which result from economic advances. Since the rate of obesity in Korean adults is increasing 3% each year, the obesity problem is gradually getting worse. Therefore, there is a need to develop a therapeutic agent or treatment method for treating and preventing obesity.

Obesity therapeutic agents, which are known to date, are broadly classified into appetite suppressants, energy consumption promoters, and fat absorption inhibitors, such as Xenical™ (Roche Pharmaceuticals, Switzerland), Reductil™ (Abbott, USA), and Exolise™ (Atopharma, France), and most obesity drugs are appetite suppressants that suppress appetite by regulating neurotransmitters associated with the hypothalamus. However, conventional therapeutic agents have low persistence of efficacy, along with side effects such as heart disease, respiratory diseases, and neurological diseases, and thus there is a need to develop more improved obesity therapeutic agents. In addition, products being currently developed also have little satisfactory therapeutic effect, and thus there is a need to develop a novel obesity therapeutic agent.

On the other hand, many efforts have been made to reduce cholesterol levels in the blood using lactic acid bacteria, which are considered safe microorganisms. *Lactobacillus*, which is a metabolite that uses sugars as an energy source, produces a large amount of lactic acid and also produces other organic acids and antibacterial substances such as bacteriocin, but does not produce indole, skatole, phenol, amines or ammonia, or the like, which are harmful to the intestines of humans or animals. Thus, *lactobacillus* is a beneficial bacterium that prevents spoilage, suppresses harmful bacteria, and exhibits physiological activity that is beneficial to humans. Among these, strains belonging to the genus *Lactobacillus* are a major member of the normal microbial community inhabiting the intestines of the human body, and have long been known to be important for maintaining a healthy digestive system and vaginal environment. According to U.S. Public Health Service guidelines, all *Lactobacillus* strains, which are currently deposited in the U.S. strain depository organization (ATCC), are classified as "Bio-safety Level 1," which is recognized as having no known potential risk of causing diseases to humans or animals.

Korean Registered Patent Publication No. 10-1471033 discloses a Weisella sp. F22 (Accession No.: KACC 91867P) strain having excellent anti-obesity activity, and Korean Registered Patent Publication No. 10-0264361 discloses a *Lactobasillus plantarum* PMO08 (KFCC-11028) strain having a cholesterol-lowering ability and deconjugation activity against 6 types of conjugated bile acids.

However, since commercially successful technologies related to *Lactobacillus* exhibiting an excellent anti-obesity effect have not yet emerged, as having conducted research on probiotics having no side effects in the body and exhibiting an excellent obesity treatment effect, the inventors of the present disclosure newly discovered a *Lactobacillus paracasei* AO356 strain, and confirmed that the strain exhibited high viability and activity in the body of animals, and exhibited an excellent effect of alleviating, preventing, or treating obesity even when the strain itself was directly added as an active ingredient of foods and medicines, and thus completed the present disclosure.

RELATED ART DOCUMENTS

Patent Documents (Patent Document 0001) Patent Document 1. Korea Registered Patent Publication No. 10-1471033
(Patent Document 0002) Patent Document 2. Korea Registered Patent Publication No. 10-0264361

SUMMARY

Provided is a *Lactobacillus paracasei* AO356 strain (KCCM12145P) having anti-obesity activity.

Provided are probiotics including the *Lactobacillus paracasei* AO356 strain (KCCM12145P) or a culture medium thereof.

Provided is a pharmaceutical composition for preventing or treating obesity, including the *Lactobacillus paracasei* AO356 strain (KCCM12145P) or a culture medium thereof.

Provided are a food composition for preventing or alleviating obesity and a food composition for alleviating inflammation caused by obesity, the compositions including the *Lactobacillus paracasei* AO356 strain (KCCM12145P) or a culture medium thereof.

Additional aspects will be set forth in part in the description which follows and, in part, will be apparent from the description, or may be learned by practice of the presented embodiments.

According to an aspect of the present disclosure, there is provided a *Lactobacillus paracasei* AO356 strain (KCCM12145P) having anti-obesity activity.

According to another aspect of the present disclosure, there are provided probiotics including the *Lactobacillus paracasei* AO356 strain (KCCM12145P) or a culture medium thereof.

According to another aspect of the present disclosure, there is provided a pharmaceutical composition for preventing or treating obesity, including the *Lactobacillus paracasei* AO356 strain (KCCM12145P) or a culture medium thereof.

The *Lactobacillus paracasei* AO356 strain (KCCM12145P) or the culture medium thereof may be included in an amount of about 0.01 wt % to about 50 wt % with respect to a total weight of the composition.

The composition may inhibit adipogenic differentiation.

The composition may induce differentiation into M2 type macrophages.

The composition may reduce body weight.

According to another aspect of the present disclosure, there is provided a food composition for preventing or alleviating obesity, including the *Lactobacillus paracasei* AO356 strain (KCCM12145P) or a culture medium thereof.

According to another aspect of the present disclosure, there is provided a food composition for alleviating inflammation caused by obesity, including the *Lactobacillus paracasei* AO356 strain (KCCM12145P) or a culture medium thereof.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
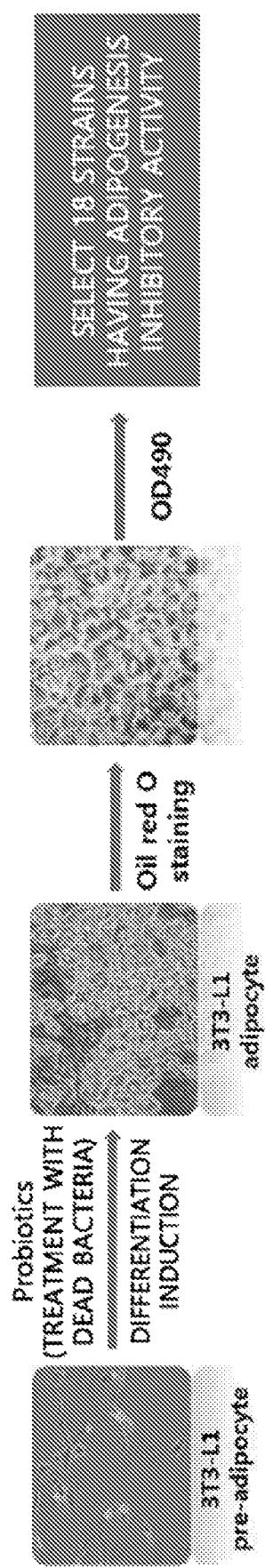
FIG. 1 is a view illustrating a series of analysis processes for selecting strains having anti-obesity activity according to Experimental Example 1 of the present disclosure.

Exemplary embodiments of the present disclosure will be described in detail with reference to the accompanying drawings. While the present disclosure is shown and described in connection with exemplary embodiments thereof, it will be apparent to those skilled in the art that various modifications can be made without departing from the spirit and scope of the present disclosure.

Hereinafter, various aspects and various embodiments of the present disclosure will be described in more detail.

One embodiment of the present disclosure relates to a *Lactobacillus paracasei* AO356 strain (KCCM12145P) having anti-obesity activity.

The *Lactobacillus paracasei* AO356 strain according to the present disclosure is a strain isolated from the human body, and is a strain deposited in the Korean Culture Center of Microorganisms on Nov. 2, 2017.

The *Lactobacillus paracasei* AO356 strain according to the present disclosure includes 16S rDNA having the nucleotide sequence set forth in SEQ ID NO: 1, and the *Lactobacillus paracasei* AO356 strain is a Gram-positive bacterium that appears purple in Gram staining and uses, as carbon sources, glucose, galactose, maltose, D-ribose, sucrose, lactose, trehalose raffinose, and the like.

In addition, the *Lactobacillus paracasei* AO356 strain may further exhibit, in addition to anti-obesity activity, an activity of inhibiting inflammation caused by obesity. When ingested via oral administration, the *Lactobacillus paracasei* AO356 strain suppresses adipogenic differentiation, induces differentiation into M2 macrophages to thereby inhibit obesity, and reduces a host's intake of dietary fat, while increasing the excretion of dietary fat, thereby reducing the body weight of a host.

In addition, the *Lactobacillus paracasei* AO356 strain of the present disclosure has excellent viability against gastric acid or bile, and thus exhibits high viability in the body of an animal, so that the strain can maintain anti-obesity activity in the body for a long time.

Also, another embodiment of the present disclosure relates to probiotics including the *Lactobacillus paracasei* AO356 strain (KCCM12145P) or a culture medium thereof.

The *Lactobacillus paracasei* AO356 strain according to the present disclosure may be used as it is in a cultured state, or may be used in the form of dry powder.

In the present disclosure, the culture medium refers to the entire medium including: a cultured strain obtained by culturing, for a certain period of time, the *Lactobacillus paracasei* AO356 strain in a known liquid medium or solid medium capable of supplying nutrients so that the *Lactobacillus paracasei* AO356 strain can grow and survive in vitro; a metabolite thereof; extra nutrients; or the like, and the culture medium also includes a culture medium from which the strain is removed after being cultured.

The culture medium may be centrifuged or filtered, or concentrated, and these processes may be performed according to the needs of one of ordinary skill in the art.

In the present disclosure, probiotics refer to intestinal flora that are beneficial to health, i.e., living microorganisms, i.e., living bacteria, which provide benefits to the health of a host. In general, probiotics are consumed as part of fermented foods such as yogurt or as dietary supplements.

The *Lactobacillus paracasei* AO356 strain of the present disclosure, which is a strain of the genus *Lactobacillus* known as probiotics, has excellent viability against gastric acid and bile, and has anti-obesity activity, and thus may be used as a probiotic.

The *Lactobacillus paracasei* AO356 strain (KCCM12145P) or the culture medium thereof may be included in an amount of about 0.01 wt % to about 50 wt % with respect to a total weight of the composition.

The composition may be administered such that the number of live bacteria of the *Lactobacillus paracasei* AO356 strain included in the composition is a concentration of less than $5 \times 10^7$ CFU, but this has to be selected depending on a patient and a situation, and the number of live bacteria in the composition is not intended to limit the scope of the present disclosure.

Another embodiment of the present disclosure relates to a pharmaceutical composition for preventing or treating obesity and a food composition for preventing or alleviating obesity, the compositions including the *Lactobacillus paracasei* AO356 strain (KCCM12145P) or a culture medium thereof.

The *Lactobacillus paracasei* AO356 strain according to the present disclosure may be used as it is in a cultured state or may be used in the form of dried powder.

In the present disclosure, the culture medium refers to the entire medium including: a cultured strain obtained by culturing, for a certain period of time, the *Lactobacillus paracasei* AO356 strain in a known liquid medium or solid medium capable of supplying nutrients so that the *Lactobacillus paracasei* AO356 strain can grow and survive in vitro; a metabolite thereof; extra nutrients; or the like, and the culture medium also includes a culture medium from which the strain is removed after being cultured. The culture medium from which the strain has been removed may be a sterilized culture medium including dead bacteria, or may be a filtrate or centrifuged supernatant from which the strain is removed by filtration or centrifugation.

The culture medium may be centrifuged or filtered, or concentrated, and these processes may be performed according to the needs of one of ordinary skill in the art.

The *Lactobacillus paracasei* AO356 strain (KCCM12145P) or the culture medium thereof is included in an amount of about 0.01 wt % to about 50 wt % with respect to the total weight of the composition, and may be directly used, may be used after concentration, or may be diluted after concentration or drying and used.

The effect of alleviating, treating or preventing obesity according to the present disclosure is expected to be obtained by the *Lactobacillus paracasei* AO356 strain that, while proliferating, inhibits the differentiation of mast cells, induces differentiation into M2 type macrophages, and reduces a host's intake of dietary fat, while increasing the excretion of dietary fat, thereby reducing the body weight of the host, and the composition may be used as it is in a liquid state, or may also be dried and powdered.

The expression "including as an active ingredient" means including the *Lactobacillus paracasei* AO356 strain or the culture medium thereof in an amount sufficient to achieve obesity-alleviating, -treating, or -preventing efficacy or activity.

The term "prevention" means all actions that inhibit or delay the onset, spread, and recurrence of obesity via administration of the composition, and the term "treatment" means all actions that improve or beneficially change the symptoms of obesity via administration of the composition.

The food composition may be prepared by formulating the composition in the form of capsules, tablets, powder, granules, liquids, pills, flakes, pastes, syrups, gels, jellies, or bars, or may be prepared into a general food form by adding the composition to food substances such as beverages, teas, spices, gum, or confectionaries, and means a food composition that has specific health effects when ingested, but has an advantage that, unlike general drugs, the food composition uses food as raw materials, and thus has no side effects that may occur when drugs are administered for a long time.

The food composition is very useful because it may be ingested daily. The amount of the *Lactobacillus paracasei* AO356 strain or the culture medium thereof added in such a food composition varies depending on the type of target food, and thus cannot be equally defined, but the strain may be added within a range that does not impair the original taste of food, and the amount of the strain generally ranges from about 0.01 wt % to about 50 wt %, preferably about 0.1 wt % to about 20 wt %, with respect to the target food. In addition, in the case of a food composition in the form of capsules, tablets, powders, granules, liquids, pills, flakes, pastes, syrups, gels, jellies, or bars, the strain is generally added in the range of about 0.1 wt % to about 100 wt %, preferably about 0.5 wt % to 80 wt %.

The food composition may include, in addition to the *Lactobacillus paracasei* AO356 strain or the culture medium thereof as an active ingredient, ingredients that are commonly added in food preparation, and examples of the ingredients include proteins, carbohydrates, fat, nutrients, a seasoning agent, and a flavoring agent. Examples of the above-described carbohydrates include general sugars such as monosaccharides, e.g., glucose and fructose; disaccharides, e.g., maltose, sucrose, and oligosaccharides; and polysaccharides, e.g., dextrin and cyclodextrin, and sugar alcohols such as xylitol, sorbitol, and erythritol.

As the flavoring agent, a natural flavoring agent (thaumatin and *stevia* extracts (e.g., rebaudioside A and glycyrrhizin) and a synthetic flavoring agent (saccharin, aspartame, and the like) may be used.

For example, when the food composition of the present disclosure is prepared as drinks and beverages, the food composition may further include, in addition to the *Lactobacillus paracasei* AO356 strain or a culture medium thereof, citric acid, liquid fructose, sugar, glucose, acetic acid, malic acid, fruit juice, various plant extracts, and the like.

In addition, the pharmaceutical composition for preventing or treating obesity including, as an active ingredient, the *Lactobacillus paracasei* AO356 strain or a culture medium thereof may be administered such that the number of live bacteria of the *Lactobacillus paracasei* AO356 strain is included at a concentration of less than $5\times10^7$, preferably $5\times10^3$ CFU to $5\times10^7$ CFU, but this has to be selected depending on a patient and a situation, and the number of live bacteria in the composition is not intended to limit the scope of the present disclosure.

In addition, the culture medium is included in the composition at a dose of 0.001 mg/kg or more, preferably 0.1 mg/kg or more, more preferably 10 mg/kg or more, even more preferably 100 mg/kg or more, still more preferably 250 mg/kg or more, and most preferably 0.1 g/kg or more. The *Lactobacillus paracasei* AO356 strain, which is a strain isolated from the human body, does not have side effects on the human body even when administered an excess dose of live bacteria, and thus, the quantitative upper limit of the *Lactobacillus paracasei* AO356 strain included in the composition of the present disclosure may be selected by one of ordinary skill in the art within an appropriate range.

The pharmaceutical composition may be prepared using a pharmaceutically acceptable and physiologically acceptable adjuvant in addition to the active ingredient, and the adjuvant includes excipients, disintegrants, sweeteners, binders, coating agents, expanding agents, lubricants, flavoring agents, or the like.

The pharmaceutical composition may be formulated by further including one or more pharmaceutically acceptable carriers, in addition to the active ingredient described above for administration.

Formulations of the pharmaceutical composition may be granules, powders, tablets, coated tablets, capsules, suppositories, liquids, syrups, juices, suspensions, emulsions, drops, injectable liquids, or the like. For example, for formulation in the form of tablets or capsules, the active ingredient may be combined with an oral, non-toxic pharmaceutically acceptable inert carrier such as ethanol, glycerol, or water. In addition, if desired or necessary, suitable binders, lubricants, disintegrants, and colorants may also be included as a mixture. Suitable binders include, but are not limited to, natural sugars such as starch, gelatin, glucose, or beta-lactose, sweeteners of corn, natural and synthetic gum such as acacia, tragacanth, or sodium oleate, sodium stearate, magnesium stearate, sodium benzoate, sodium acetate, and sodium chloride. Disintegrants include, but are not limited to, starch, methyl cellulose, agar, bentonite, and xanthan gum.

Pharmaceutically acceptable carriers in compositions formulated as liquid solution are sterile and biocompatible, and as the carrier, saline, sterile water, Ringer's solution, buffered saline, an albumin injection solution, a dextrose solution, a maltodextrin solution, glycerol, ethanol, and a mixture of one or more of these components may be used. As necessary, other general additives such as antioxidants, buffers, and bacteriostatic agents may be added. In addition, diluents, dispersants, surfactants, binders, and lubricants may be additionally added to formulate into injectable formulations such as aqueous solutions, suspensions, and emulsions, pills, capsules, granules, or tablets.

Furthermore, the compositions of the present disclosure may be formulated according to each disease or ingredient using methods disclosed in Remington's Pharmaceutical Science, Mack Publishing Company, Easton Pa. by appropriate methods in the art.

The pharmaceutical composition may be administered orally or parenterally, and in the case of parenteral administration, the pharmaceutical composition may be administered via intravenous injection, subcutaneous injection, intramuscular injection, intraperitoneal injection, transdermal administration, or the like, and oral administration is preferably used.

A suitable dose of the pharmaceutical composition may vary depending on factors, such as formulation method, administration method, the age, body weight, and gender of a patient, pathologic conditions, diet, administration time, administration route, excretion speed, and reaction sensitivity, and ordinarily skilled doctors can easily determine and prescribe an effective dose for targeted treatment or prevention. According to an exemplary embodiment, a daily dose of the pharmaceutical composition ranges from about 0.001 g/kg to about 10 g/kg.

The pharmaceutical composition may be formulated using a pharmaceutically acceptable carrier and/or an excipient by a method, which may be easily carried out by one of ordinary skill in the art to which the present disclosure pertains, to be prepared in a unit dose form or to be contained in a multi-dose container. In this regard, the formulation may be a solution in oil or an aqueous medium, a suspension, an emulsion, an extract, powder, granules, tablets, or capsules, and may further include a dispersing agent or a stabilizing agent.

Furthermore, the present invention provides a method for preventing, alleviating or treating obesity, comprising administering a composition containing the *Lactobacillus paracasei* AO356 strain (KCCM12145P) of claim 1 or a culture medium thereof to subject in need thereof.

In addition, the present n provides a method for alleviating inflammation caused by obesity, comprising administering a compositon containing the *Lactobacillus paracasei* AO356 strain (KCCM12145P) of claim 1 or a culture medium thereof to subject in need thereof.

The term "subject" used herein refers to a target in need of treatment, and more specifically, a mammal such as a human or a non-human primate, a mouse, a rat, a dog, a cat, a horse, or a cow.

Hereinafter, the present disclosure will be described in further detail with reference to the following examples and the like. However, these examples and the like should not be construed as limiting the scope and content of the present disclosure. In addition, based on the disclosure of the present disclosure including the following examples, it is obvious that those of ordinary skill in the art can easily carry out the present disclosure in which experimental results are not specifically presented, and it is also obvious that these changes and modifications fall within the appended claims.

In addition, the experimental results presented below are only representative experimental results of the examples and comparative examples, and the effects of various embodiments of the present disclosure, which are not explicitly presented below, are described in detail in the corresponding parts.

Example 1. 36 Strains

To select a candidate group of probiotics having anti-obesity activity, 36 strains (see Table 1) derived from the human body were collected, and each strain was isolated and identified, and shown in Table 1. Each strain was cultured in MRS medium (Difco, 288110) at 37° C. for 18 hours to 24 hours.

TABLE 1

| No. | Strain name |
| --- | --- |
| 1 | Lactobacillus sakei subsp. Sakei |
| 2 | Streptococcus infantarius subsp. Coli |
| 3 | Bacillus licheniformis |
| 4 | Bacillus siamensis |
| 5 | Lactobacillus sakei subsp. Carnosus |
| 6 | Enterococcus faecalis |
| 7 | Enterococcus hirae |
| 8 | Carnobacterium maltaromaficum BA |
| 9 | Lactobacillus reuteri |
| 10 | Enterococcus faecium |
| 11 | Enterococcus faecium |
| 12 | Enterococcus faecium |
| 13 | Lactobacillus fermentum |
| 14 | Lactobacillus mucosae |
| 15 | Lactobacillus paracasei AO365 |
| 16 | Lactobacillus acidilacfici |
| 17 | Lactobacillus zeae |
| 18 | Enterococcus faecium |
| 19 | Lactobacillus reuteri |
| 20 | Lactobacillus johnsonii |
| 21 | Lactobacillus pentosus |
| 22 | Lactobacillus gassei |
| 23 | Lactobacillus ruminis |
| 24 | Lactobacillus mesenteroides subsp. Mesenteroides |
| 25 | Obesumbacterium proteus |
| 26 | D29 |
| 27 | I01-7 |
| 28 | I02-4 |
| 29 | M40a |
| 30 | Lactobacillus acidophilus |
| 31 | Lactobacillus rhamnosus |
| 32 | Pediococcus pentosaceus |
| 33 | Bifidobacterium lactis |
| 34 | Bifidobacterium breve |
| 35 | Lactobacillus acidophilus |
| 36 | Lactobacillus intestinalis |

Experimental Example 1. Selection of Strains Having Adipogenesis Inhibitory Activity To evaluate the anti-obesity efficacy of the upper tier candidate strains, the ability to inhibit the differentiation of pre-adipocytes (3T3-L1 cells) into adipocytes (Example 1) and the ability to regulate macrophages (splenic macrophages isolated from mice) (Example 2) were analyzed and compared.

(1) Experimental Method

The accumulation of lipids in adipocytes is the most representative characteristic of obesity. Adipocytes are formed by the differentiation of pre-adipocytes derived from stem cells, and while 3T3-L1 cells (pre-adipocytes) differentiate into adipocytes, intracellular fat globules are formed through morphological and biochemical changes, and as the differentiation progresses, the size of fat globules increases. Since most fat globules consist of proteins such as triglycerides and perilipin A, the degree of fat differentiation may be confirmed by measuring the intracellular content of triglycerides.

Thus, 3T3-L1 cells, which are representative pre-adipocytes, were treated with each of the upper tier candidate strains, differentiation was induced, and the intracellular content of triglycerides (TG) was measured to evaluate the activity of inhibiting adipogenesis.

For the above-described TG content measurement experiment, culturing of cells was maintained for at least 8 days or longer. In addition, to exclude the impact of the upper tier candidate strains on the growth of 3T3-L1 cells, the upper tier candidate strains were treated in a dead form.

Prior to the TG experiment, as a result of confirming cytotoxicity through water soluble tetrazolium (WST) analysis for the upper tier candidate strains, cytotoxicity was not shown at a concentration of $1\times10^7$ CFU to $1\times10^6$ CFU, and thus in order to measure adipogenesis inhibitory activity, the concentration of dead bacteria of the treated upper tier candidate strains was fixed at $1\times10^7$ CFU/well to $1\times10^6$ CFU/well.

Specifically, to investigate the effect of each candidate strain on the degree of lipid accumulation in a fat differentiation process, Oil Red O staining was performed according to the methods of Negrel and Dani. 100% confluent 3T3-L1 cells were treated with $1\times10^7$ CFU/mL of each of the 36 upper tier candidate strains, and cultured in MDI medium (DMEM+FBS+PS+Insulin+Dexamethasone+IBMX+Insulin). After 10 days of differentiation, the culture medium was removed, followed by washing with PBS and then fixing with 10% formaldehyde for 10 minutes. The 10% formaldehyde was removed and saturated formaldehyde was added again to fix the cells for 1 hour or more. Thereafter, 60% isopropanol was added and immediately removed, followed by washing with distilled water, and fat globules were stained with a solution for Oil red O staining for 30 minutes, and then washed with distilled water. The intracellular lipid accumulation of the stained fat globules was observed using a microscope and photographed to visually observe the effect of 36 strains on lipid accumulation during fat differentiation. To confirm the accumulated fat, the Oil red O dye was eluted by adding isopropanol in a dry state, and then absorbance at 490 nm was measured using a multi-plate reader. At this time, isopropanol was used as a blank.

(2) Conclusion

Figure 2:
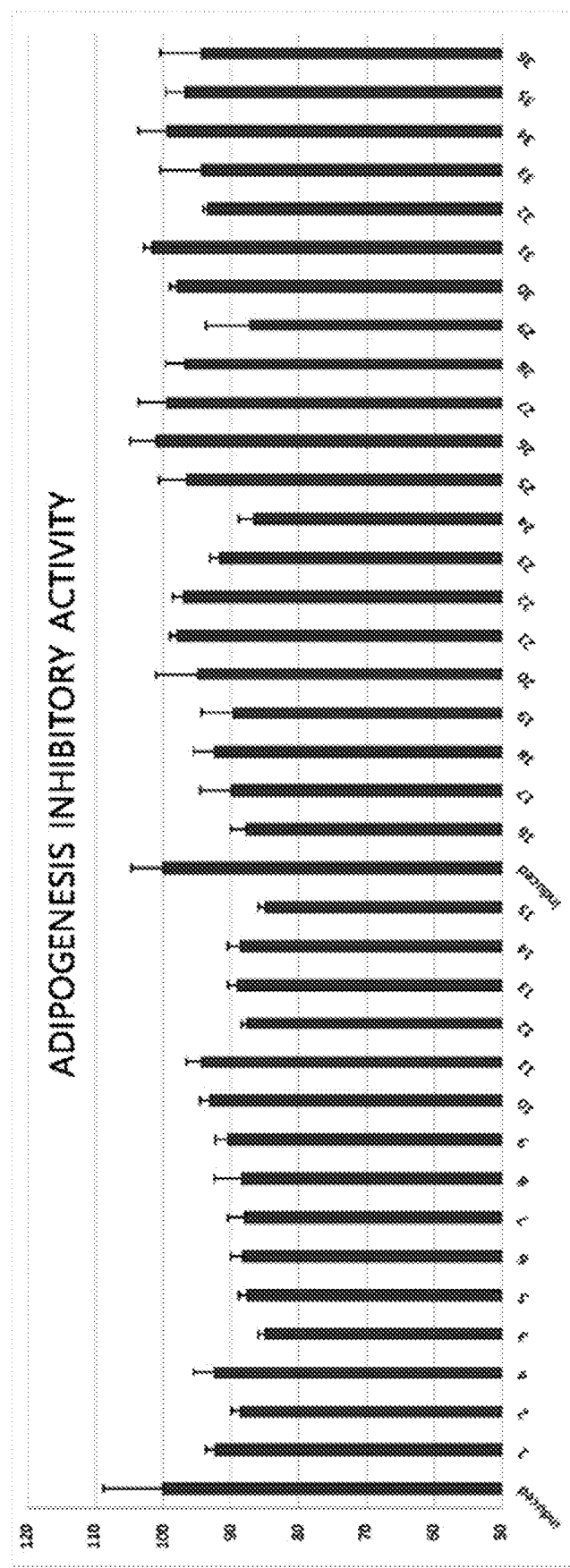
FIG. 2 is a graph showing the lipid accumulation of each of 36 strains measured using Oil red O staining according to Experimental Example 1 of the present disclosure.

FIG. 1 is a view illustrating a series of analysis processes for selecting strains having anti-obesity activity according to Experimental Example 1 of the present disclosure. FIG. 2 is a graph showing the lipid accumulation of each of 36 strains measured using Oil red O staining according to Experimental Example 1 of the present disclosure.

As illustrated in FIG. 2, as a result of comparing the intracellular contents of triglycerides (TG) of the 36 strains, a 10% or more decrease in TG content was confirmed in strain Nos. 2, 3, 5, 6, 7, 8, 12, 13, 15, 16, 21, 24, 28, and 29, and it was confirmed that, among these, strain Nos. 15 and 21 exhibited the greatest adipogenesis inhibitory activity.

Experimental Example 2. Evaluation of Regulatory Ability of Macrophages (Splenic Macrophages Isolated from Mice)

In adipose tissue, there are macrophages that regulate inflammatory responses, in addition to adipocytes. Thus, when obesity occurs, chronic inflammation or diabetes is accompanied by macrophages present in adipose tissue.

Under normal conditions, M2 type macrophages are present in adipose tissue, and these are anti-inflammatory macrophages that alleviate inflammation and have maintenance and protective activity so as not to exhibit insulin resistance. In contrast, in the case of obesity, macrophages infiltrate into adipose tissue, and M2 type macrophages are switched into M1 type macrophages. M1 type macrophages are inflammatory macrophages and are known to produce chemicals called pro-inflammatory cytokines and chemokines. For example, M1 type macrophages induce the production of cytokines such as IL-1beta, TNF-alpha, IL-6, and IL-12, causing inflammation and promoting insulin resistance.

Thus, to prevent diseases accompanied by obesity, such as inflammation and diabetes, the degree of conversion from M1 type into M2 type macrophages and whether to induce differentiation from M0 type macrophages into M2 type macrophages were analyzed to evaluate the ability of each strain to regulate macrophages.

(1) Experimental Method

To select strains capable of regulating macrophages, spleens were isolated from mice, and then splenocytes were isolated, and since various immune cells such as T cells and B cells are present in splenocytes, only CD11b and macrophages were isolated using an MACS system to conduct an experiment. The isolated macrophages were dispensed into a 96 well plate at a density of $1\times10^6$ cells/well, and then cultured for 2 hours or longer, and when the macrophages were stably adhered to the bottom of each well, 100 ng/ml of LPS and each of $3\times10^7$ CFU/well of 36 strains (dead or live form) were added. After 48 hours, the supernatant was recovered and the secretion amounts of produced IL-12 and IL-10 were measured by ELISA. At this time, IL-12 is an identification factor for M1 type macrophages, and IL-10 is an identification factor for M2 type macrophages.

Figure 3:
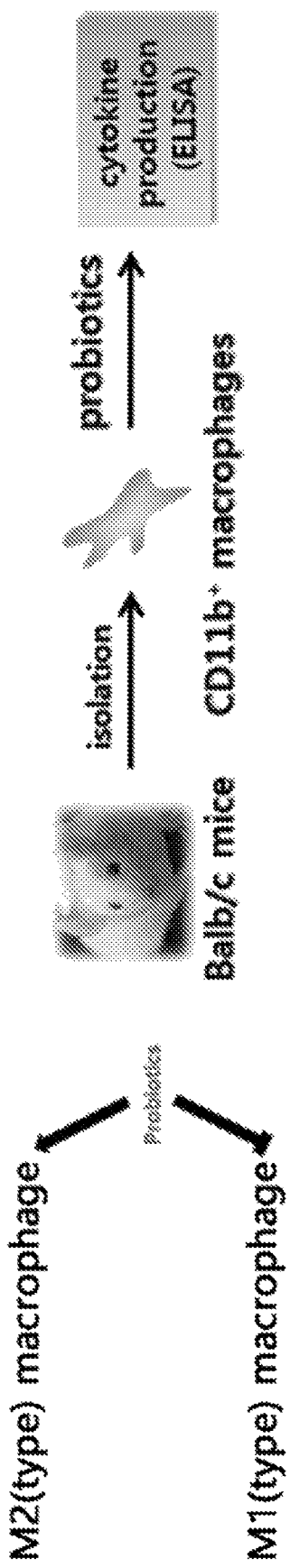
FIG. 3 is a view illustrating a series of analysis processes for selecting strains having anti-obesity activity according to Experimental Example 2 of the present disclosure.
Figure 4:
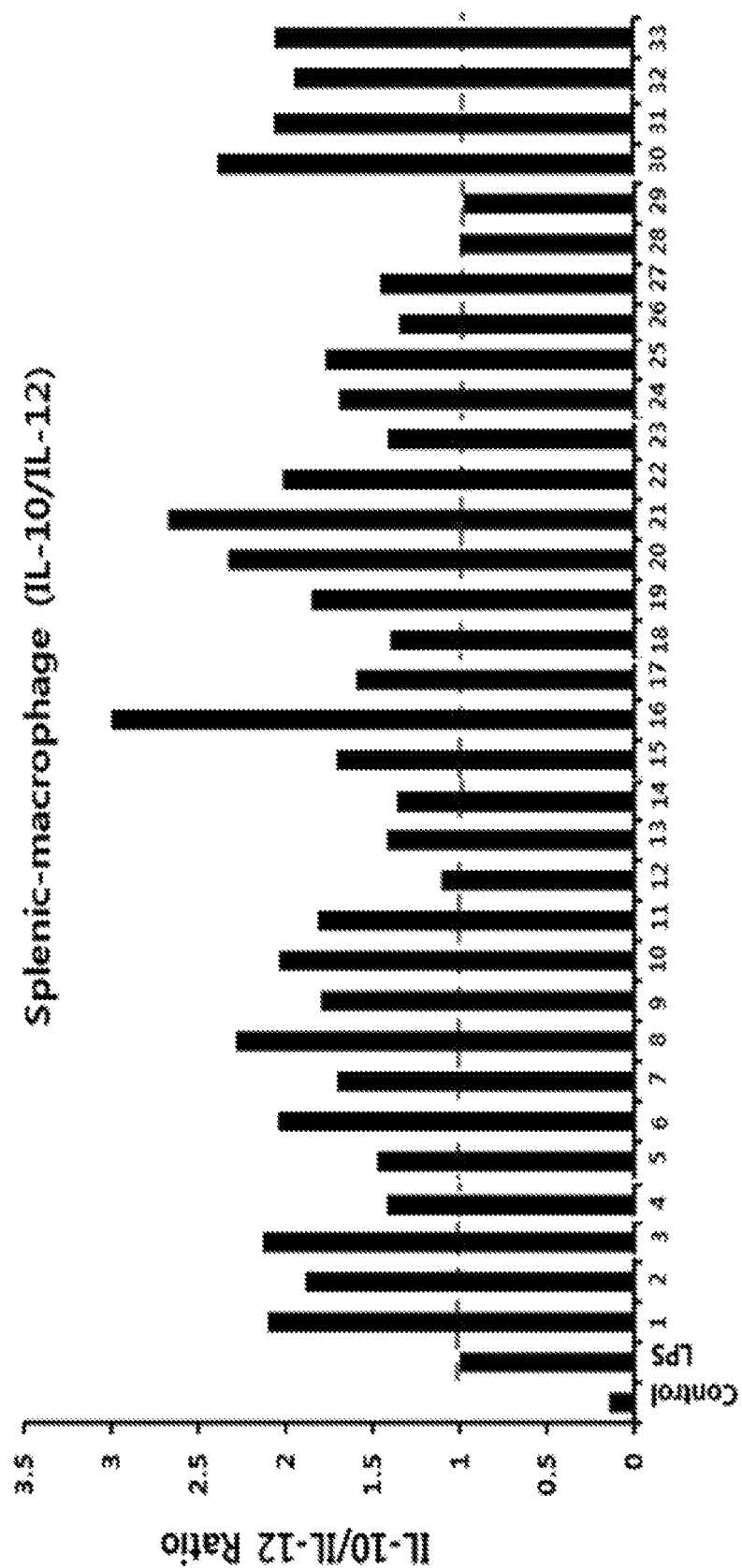
FIG. 4 is a graph showing the results of measuring cytokine secretion (%) in macrophages when treated with each of 36 dead strains according to Experimental Example 2 of the present disclosure.
Figure 5:
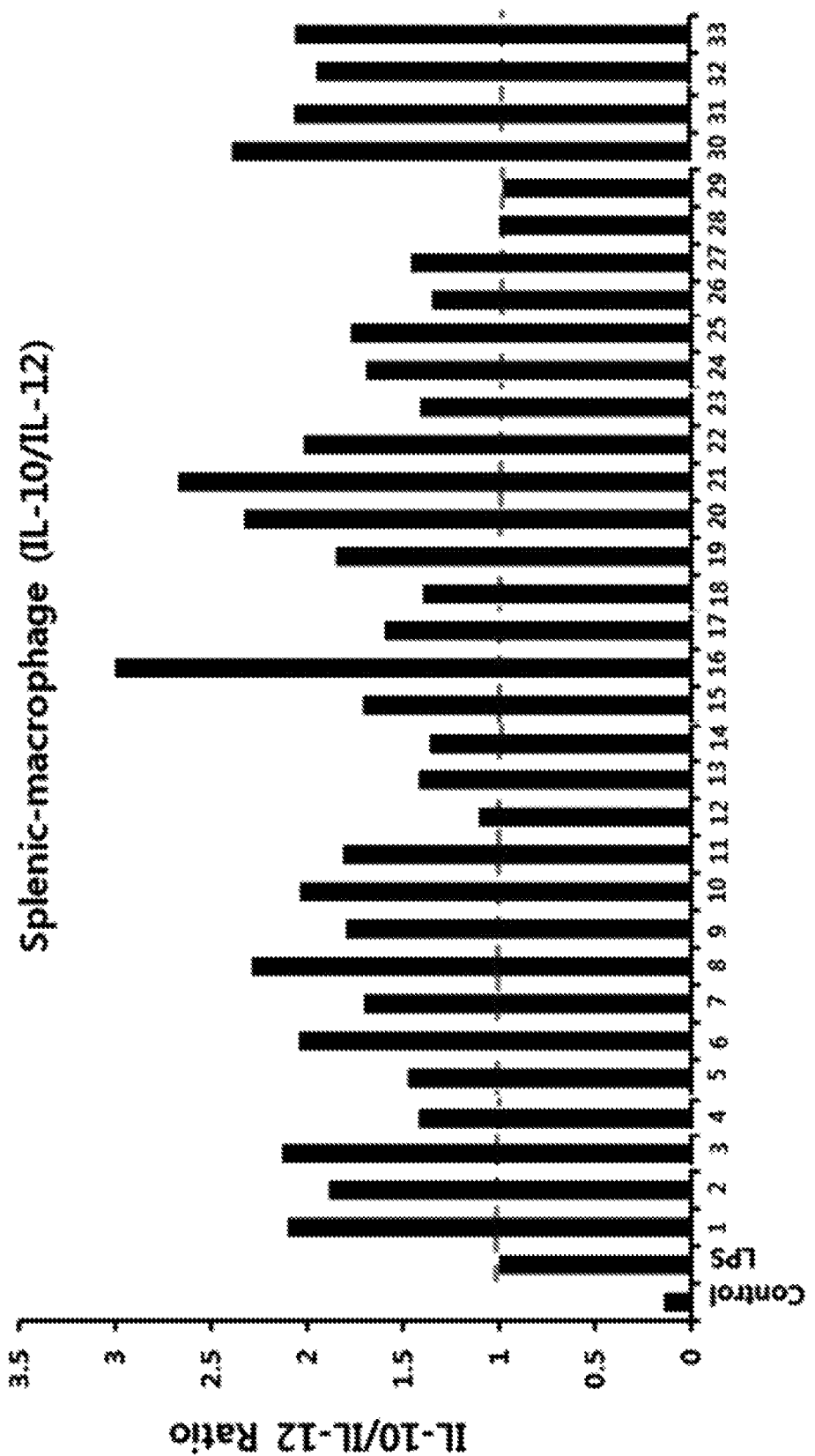
FIG. 5 is a graph showing the results of measuring a ratio of IL/10 to IL-12 in macrophages when treated with each of 36 dead strains according to Experimental Example 2 of the present disclosure.
Figure 6:
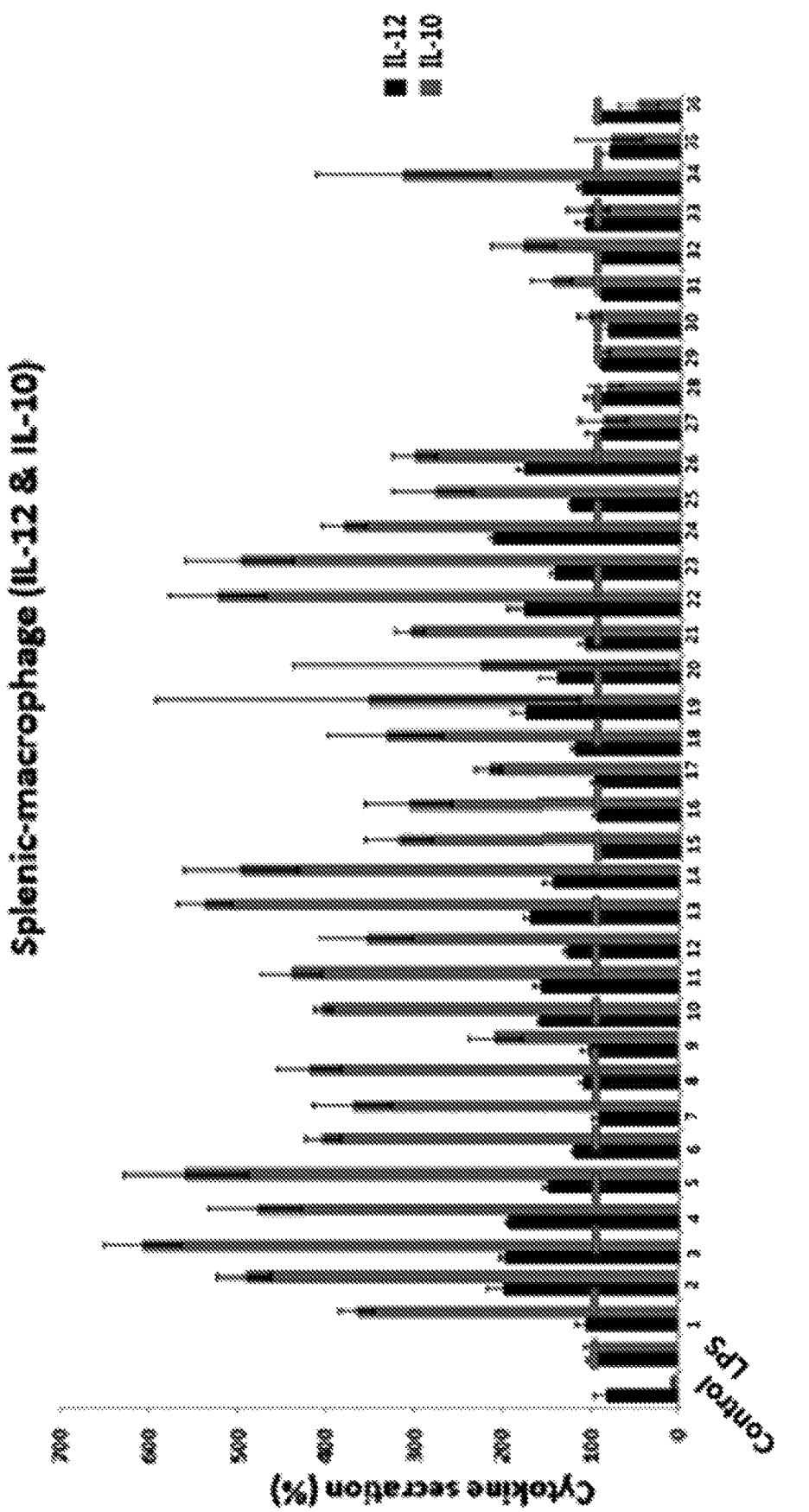
FIG. 6 is a graph showing the results of measuring cytokine secretion (%) in macrophages when treated with each of 36 live strains according to Experimental Example 2 of the present disclosure.
Figure 7:
FIG. 7 is a graph showing the results of measuring a ratio of IL-10 to IL-12 in macrophages when treated with each of 36 live strains according to Experimental Example 2 of the present disclosure.

FIG. 3 is a view illustrating a series of analysis processes for selecting strains having anti-obesity activity according to Experimental Example 2 of the present disclosure. FIG. 4 is a graph showing the results of measuring cytokine secretion (%) in macrophages when treated with each of 36 dead strains according to Experimental Example 2 of the present disclosure. FIG. 5 is a graph showing the results of measuring a ratio of IL/10 to IL-12 in macrophages when treated with each of 36 dead strains according to Experimental Example 2 of the present disclosure. FIG. 6 is a graph showing the results of measuring cytokine secretion (%) in macrophages when treated with each of 36 live strains according to Experimental Example 2 of the present disclosure. FIG. 7 is a graph showing the results of measuring a ratio of IL-10 to IL-12 in macrophages when treated with each of 36 live strains according to Experimental Example 2 of the present disclosure.

Referring to FIGS. 4 and 5, it was confirmed that, upon treatment with dead bacteria, 12 strains (strain Nos.: 1, 3, 6, 8, 10, 16, 20, 21, 22, 30, 31, and 33) exhibited a 2-fold or more increase in the IL-10/IL-12 ratio.

As illustrated in FIGS. 6 and 7, it was confirmed that, upon treatment with live bacteria, a total of 11 strains (strains Nos.: 1, 3, 5, 6, 7, 8, 13, 14, 15 16, and 23) exhibited a three-fold or more increase in the IL-10/IL-12 ratio.

From among the strains identified based on the above-described results, strains exhibiting both fat differentiation inhibitory activity and the ability to regulate macrophages although one or the other was not excellent were preferentially selected, and as a result, a total of 4 strains were selected. Specifically, strains 3 and 6 were selected because it was confirmed that they had adipogenesis inhibitory activity in vitro and exhibited the highest IL-10/IL-12 ratio, and strain 13 was selected because it was confirmed that it exhibited both adipogenesis inhibitory activity and macrophage regulatory activity in vitro.

In addition, strain 15, which is *Lactobacillus paracasei* AO356, was selected because it was confirmed that the strain exhibited the strongest fat differentiation inhibitory activity and had a relatively high IL10/IL12 ratio.

(3) Conclusion

Taken together the results of Experimental Examples 1 and 2, 4 strains (strain Nos.: 3, 6, 13, and 15) exhibiting excellent adipogenesis inhibitory activity and excellent regulatory activity against macrophages were selected, and to secondarily select, from among the selected 4 strains, strains exhibiting excellent anti-obesity activity even in vivo, in vivo anti-obesity activities were compared through an in-vivo experiment, which will be described below.

Experimental Example 3. Confirmation of Effect of Anti-Obesity Activity of Selected 4 Strains Through Animal Experiment A. Experimental Animals and Experimental Groups 6-week-old male C57BL/6 mice were purchased from Central Lab Animal Inc. and used as experimental animals, and were raised under 12 hour light/dark conditions at a temperature of 20±2° C. and a humidity of 55±5%. After purchase, the experimental animals were acclimatized for 2 weeks, and then grouped into 5 mice per group and set as experimental groups as shown in Table 2.

TABLE 2

| Classification (N = 5) | Experimental groups |
| --- | --- |
| Normal diet | Normal control fed normal feed (ND, 10% fat), orally administered 100 µl/head of PBS 5 times a week for 8 weeks |
| High fat diet | Negative control (HFD, 45% fat) fed high fat feed for induction of obesity, orally administered 100 µl/head of PBS 5 times a week for 8 weeks |
| A | After high fat feed for inducing obesity was ingested, $10^8$ CFU/head of strain No. 3 (*Bacillus licheniformis*) was orally administered five times a week for 0-4 weeks, and then $5\times10^8$ CFU/head thereof was orally administered five times a week for 5-8 weeks |
| B | After high fat feed for inducing obesity was ingested, $10^8$ CFU/head of strain No. 6 (*Enterococcus faecalis*) was orally administered five times a week for 0-4 weeks, and then $5\times10^8$ CFU/head thereof was orally administered five times a week for 5-8 weeks |
| C | After high fat feed for inducing obesity was ingested, $10^8$ CFU/head of strain No. 13 (*Lactobacillus fermentum*) was orally administered five times a week for 0-4 weeks, and then $5\times10^8$ CFU/head thereof was orally administered five times a week for 5-8 weeks |
| D | After high fat feed for inducing obesity was ingested, $10^8$ CFU/head of strain No. 15 (*Lactobacillus paracasei* AO356) was orally administered five times a week for 0-4 weeks, and then $5\times10^8$ CFU/head thereof was orally administered five times a week for 5-8 weeks |

Figure 8:
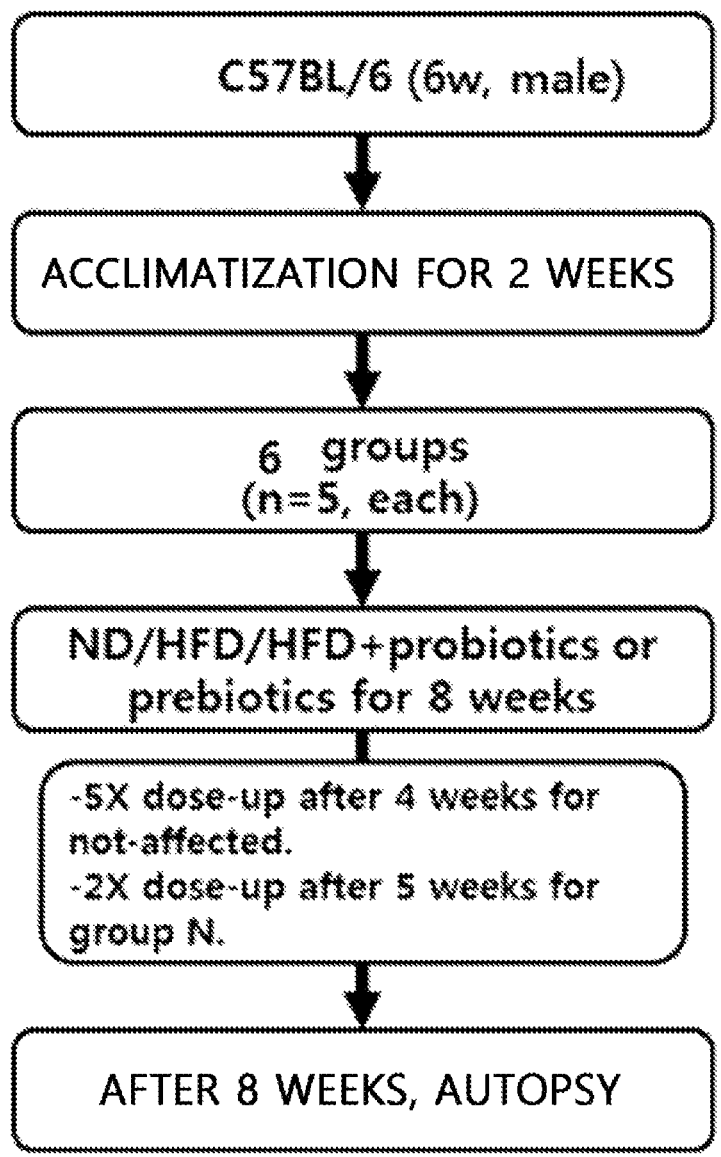
FIG. 8 is a flowchart illustrating a process of setting experimental animals and experimental groups according to Experimental Example 3 of the present disclosure.

For all experimental groups, except for Normal diet and High fat diet, feed was mixed with each strain, and then the mixture of the feed and the strain was orally administered. FIG. 8 illustrates a process of setting experimental animals and experimental groups according to Experimental Example 3 of the present disclosure.

B. Body Weight, Feed Intake, and Drinking Water Volume

For all experimental groups, the body weight change (g), feed intake (g), and drinking water volume (ml) of experimental animals were measured from the time of feeding feed until the experimental animals were sacrificed. Feed intake and water intake were measured three times a week, cages were changed twice a week, and body weight was measured once a week for comparison.

Figure 9:
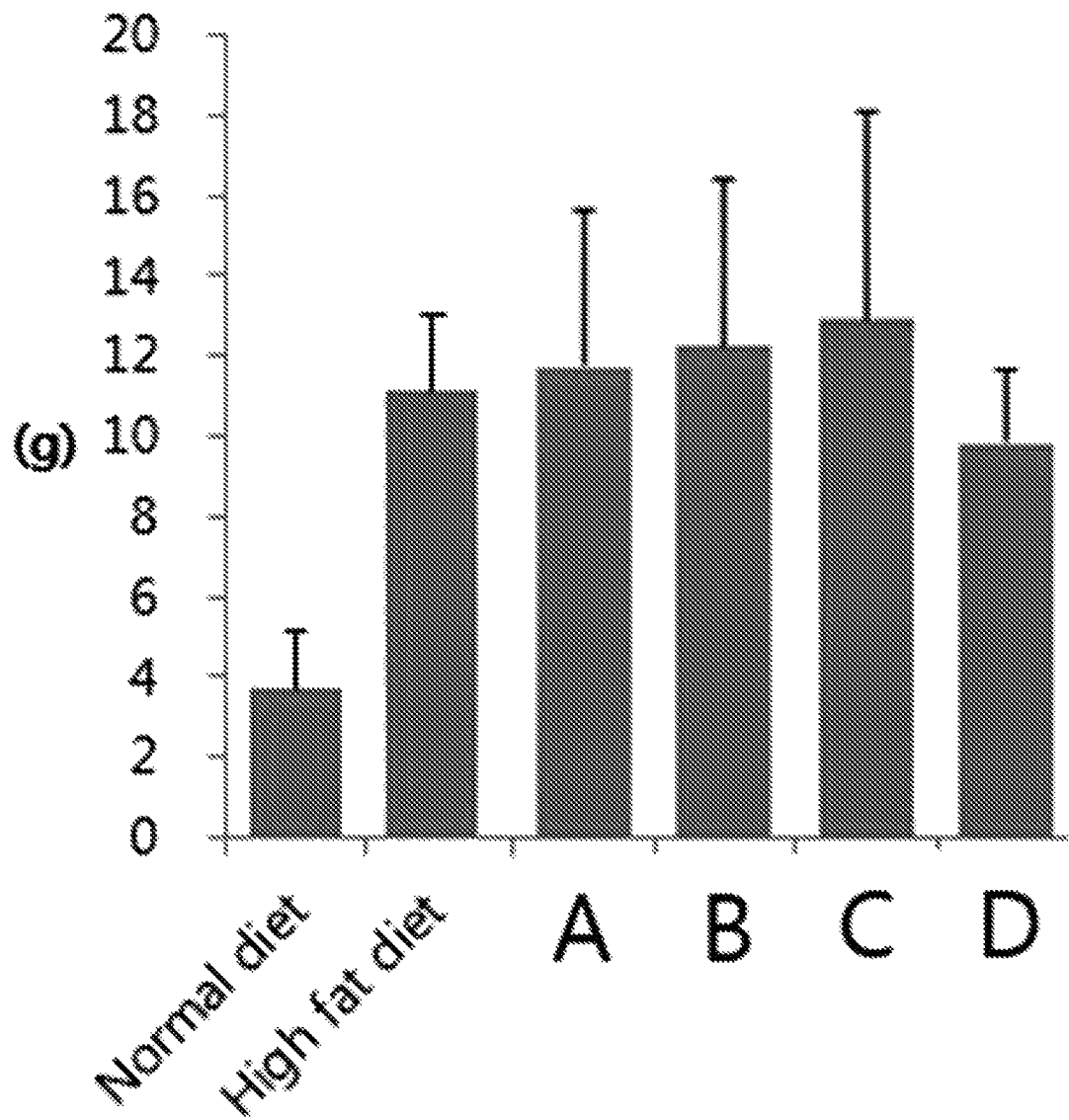
FIG. 9 is a graph showing the results of measuring a body weight change in each experimental group according to Experimental Example 3 of the present disclosure.

FIG. 9 is a graph showing the results of measuring a body weight change in each experimental group. As illustrated in this drawing, a decrease in weight gain was clearly confirmed in strain 15, i.e., *Lactobacillus paracasei* AO356.

Experimental Example 4. Identification of Selected Strain 16S rDNA Analysis

The finally selected strain was subjected to genetic analysis of 16S rDNA, which is a bacterial base conservation sequence, using universal bacterial primers (518F, 800R) for PCR (SEQ ID NO: 1). The results were analyzed using NCBI Blast.

The inventors named *Lactobacillus paracasei* AO356 "*Lactobacillus paracasei* AO356 (KCCM12145P:)" and deposited the strain in the Korean Culture Center of Microorganisms on Nov. 2, 2017.

Depository Name: Korean Culture Center of Microorganisms (overseas)

Accession No.: KCCM12145P

Date of Deposit: 20171102

Experimental Example 5. Confirmation of Effect of Anti-Obesity Activity of Finally Selected AO356 Strain in Animal Experiment A. Strain Culture To produce the *Lactobacillus paracasei* AO356 strain, which was finally selected, the *Lactobacillus paracasei* AO356 strain was streaked and inoculated onto a solid medium (Lactobacilli MRS Agar; BD Difco Co, USA) and cultured at 37° C. for 24 hours. During the culture process, it was thoroughly checked whether contamination occurred in the bacteria and a single colony was formed, and then the next experiment was conducted. After the culture was completed, colonies were collected from each solid medium, which was then inoculated into 5 mL of a liquid medium (Lactobacilli MRS broth; BD Difco Co, USA) and cultured at 37° C. and 140 rpm for 24 hours, and then the colonies were inoculated at 1% (v/v) into 200 mL of other prepared liquid media (Lactobacilli MRS broth; BD Difco Co, USA), thereby increasing bacteria stepwise. The activated *Lactobacillus paracasei* AO356 strain was subjected to 2.4 L-5 L main culture, incubated at 37° C. and 140 rpm for 24 hours, and then centrifuged (Avanti J-E, Beckman Coulter, USA) at 6,000 rpm and 4° C. for 15 minutes to recover the colonies. The recovered colonies were washed twice with sterile 0.85% physiological saline, and then lyophilized (FDCF-12003, OPERON, Korea), and powdered and stored at −80° C. until use.

B. Experimental Animals and Experimental Groups 6-week-old male C57BL/6 mice were purchased from Central Lab Animal Inc. and used as experimental animals, and were raised under 12 hour light/dark cycles at a temperature of 20±2° C. and a humidity of 55±5%. After purchase, the experimental animals were acclimatized for 2 weeks, and then grouped into 10 mice per group according to randomized complete block design and set as experimental groups as shown in Table 3.

During the acclimatization period, for the uniformity of intestinal microbial flora in the animal model, litter was mixed at 2-3 day intervals. Subsequently, the animals were grouped into 10 mice per experimental group, and a normal diet (ND) group was fed a normal diet and the remaining groups were fed a high fat diet (Rodent diet with 45% kcal Fat, Research Diets, USA). The *Lactobacillus paracasei* AO356 strain was weighed in accordance with a concentration of 5×10$^7$ CFU/head, and then suspended in sterile PBS, and orally administered 5 times a week for 10 weeks at a certain time.

At the end of the experimental period, the experimental animals were fasted for 12 hours or longer, and then blood was collected through retro-orbital blood collection and left at room temperature for 30 minutes or longer, followed by centrifugation at 1,690×g for 10 minutes to separate serum, and the serum was used in an experiment. The liver tissue, epididymal fat tissue, retroperitoneal fat tissue, inguinal fat tissue, and interscapular brown adipose tissue were extracted and washed with saline to remove moisture, and white fat attached to the interscapular brown fat tissue was removed, and then the weight of each fat was measured.

TABLE 3

| Classification (N = 10) | Experimental groups |
|---|---|
| ND | Normal control fed normal diet (ND, 10% fat), orally administered 100 μl/head of PBS 5 times a week for 10 weeks |
| HFD | Negative control fed high fat feed for inducing obesity (Rodent diet with 45% kcal Fat, Research Diets, USA), orally administered 100 μl/head of PBS 5 times a week for 10 weeks |
| *L. paracasei* AO356 | After high fat feed for inducing obesity was ingested, 5 × 10$^7$ CFU/head of finally selected *Lactobacillus paracasei* AO356 strain was orally administered 5 times a week for 10 weeks |

C. Body Weight, Feed Intake, and Drinking Water Volume

For all experimental groups, the body weight change (g), feed intake (g), and drinking water volume (ml) of experimental animals were measured from the time of feeding feed until the experimental animals were sacrificed. Feed intake and water intake were measured every day, cages were changed twice a week, and body weight was measured once a week for comparison.

Figure 10:
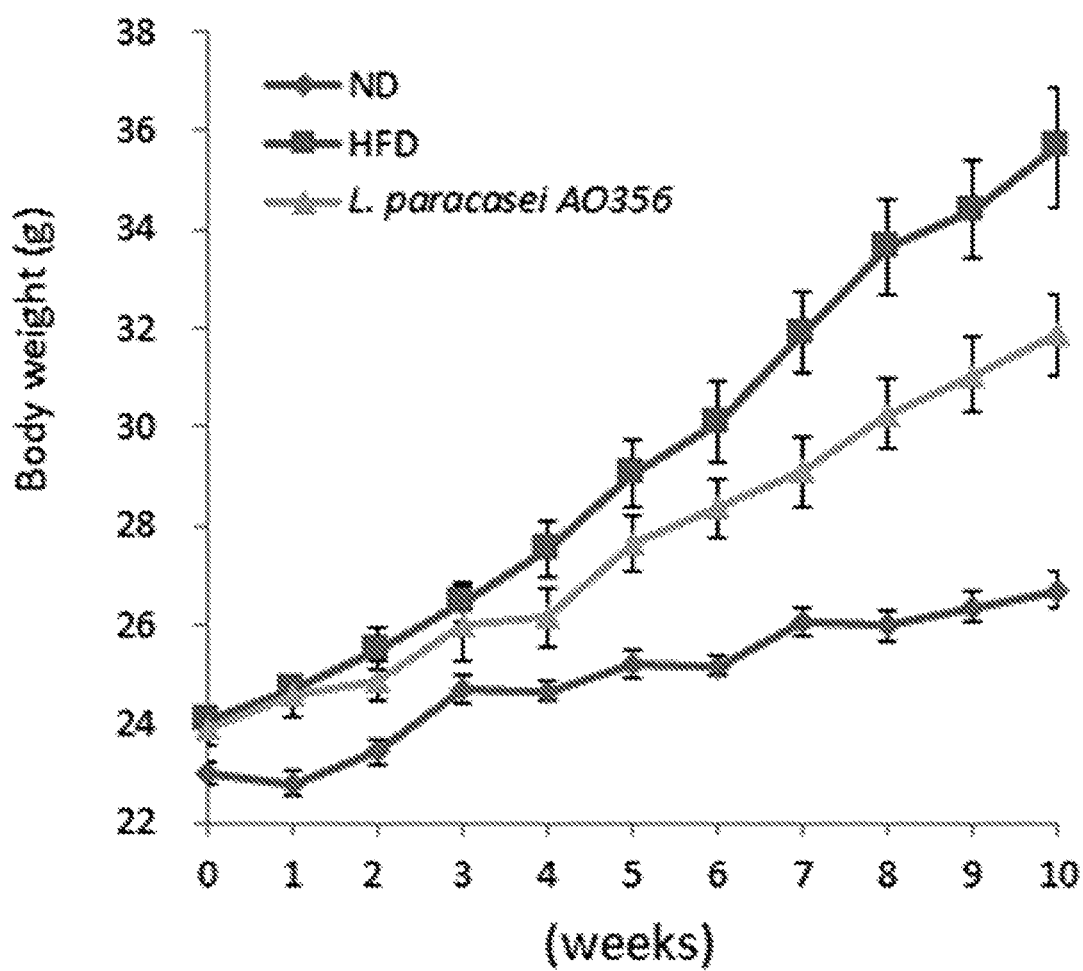
FIG. 10 is a graph showing the results of measuring a body weight change according to week in each experimental group according to Experimental Example 5 of the present disclosure.
Figure 11:
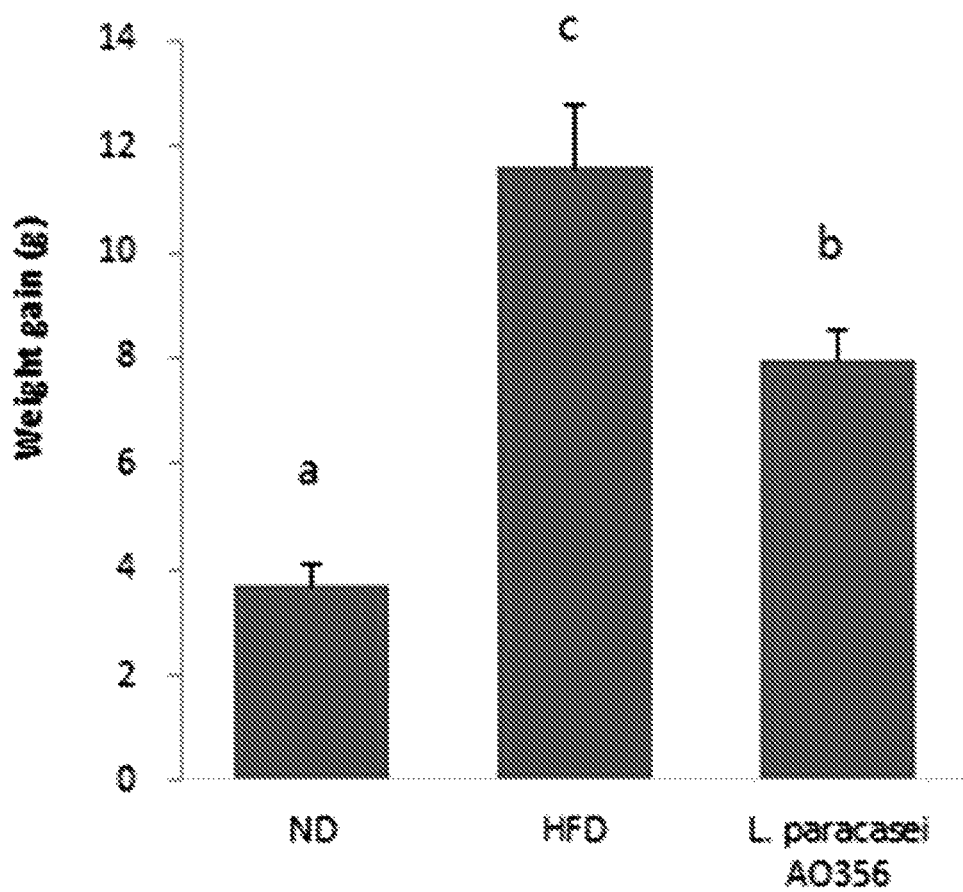
FIG. 11 is a graph showing the results of analyzing weight gain in each experimental group according to Experimental Example 5 of the present disclosure.
Figure 12A:
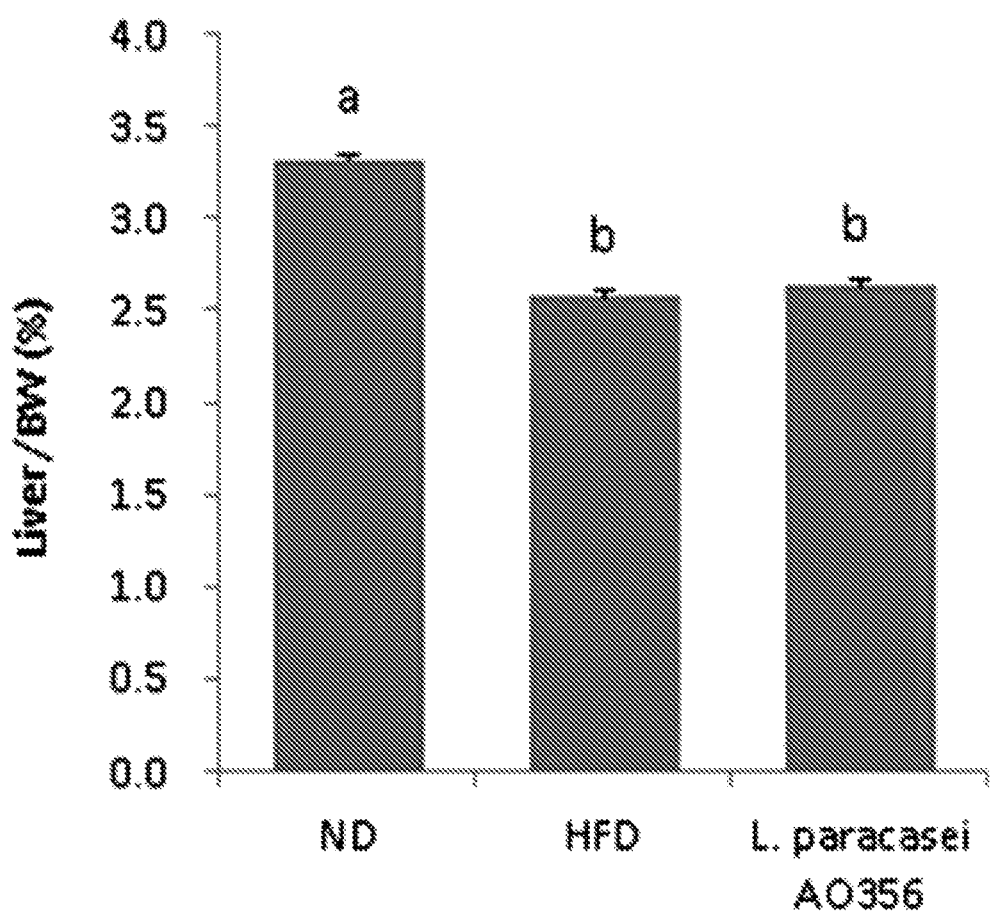
FIGS. 12A-E are a set of graphs showing the results of measuring fat weights of, with respect to body weight, the liver (A), epididymal fat tissue (B), retroperitoneal fat tissue (C), inguinal fat tissue (D), and interscapular brown adipose tissue (E), in each experimental example according to Experimental Example 5 of the present disclosure.
Figure 12B:
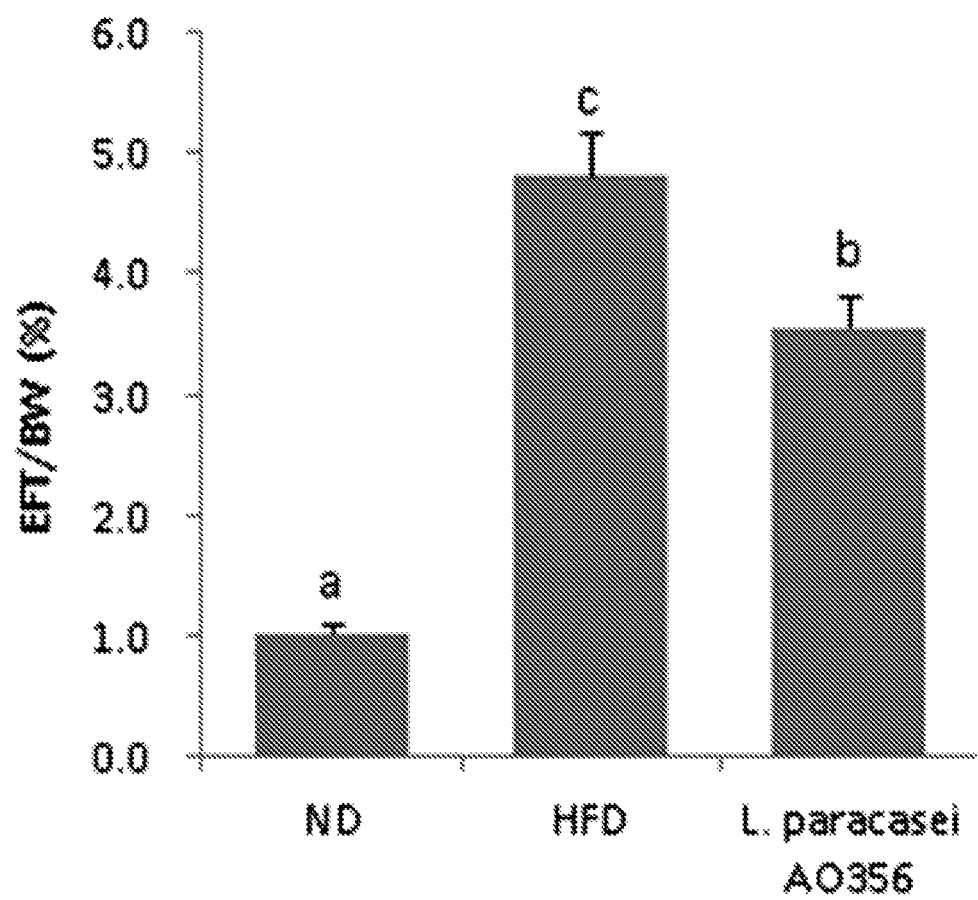
Figure 12C:
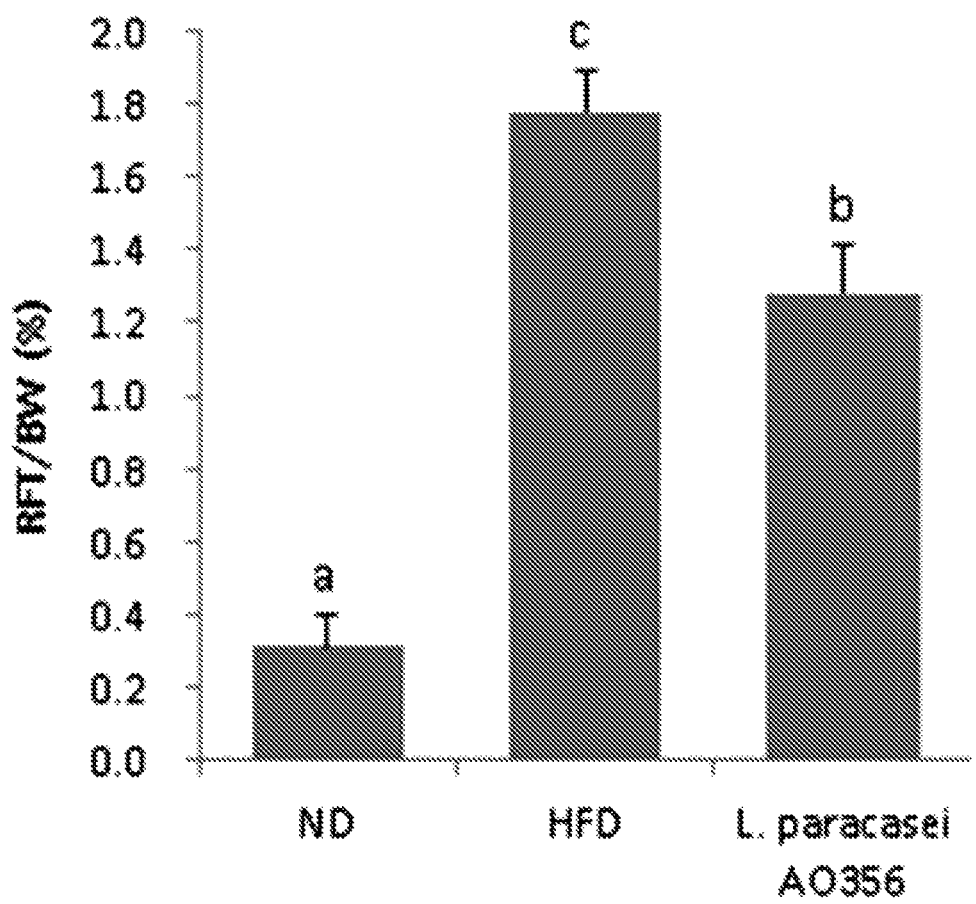
Figure 12D:
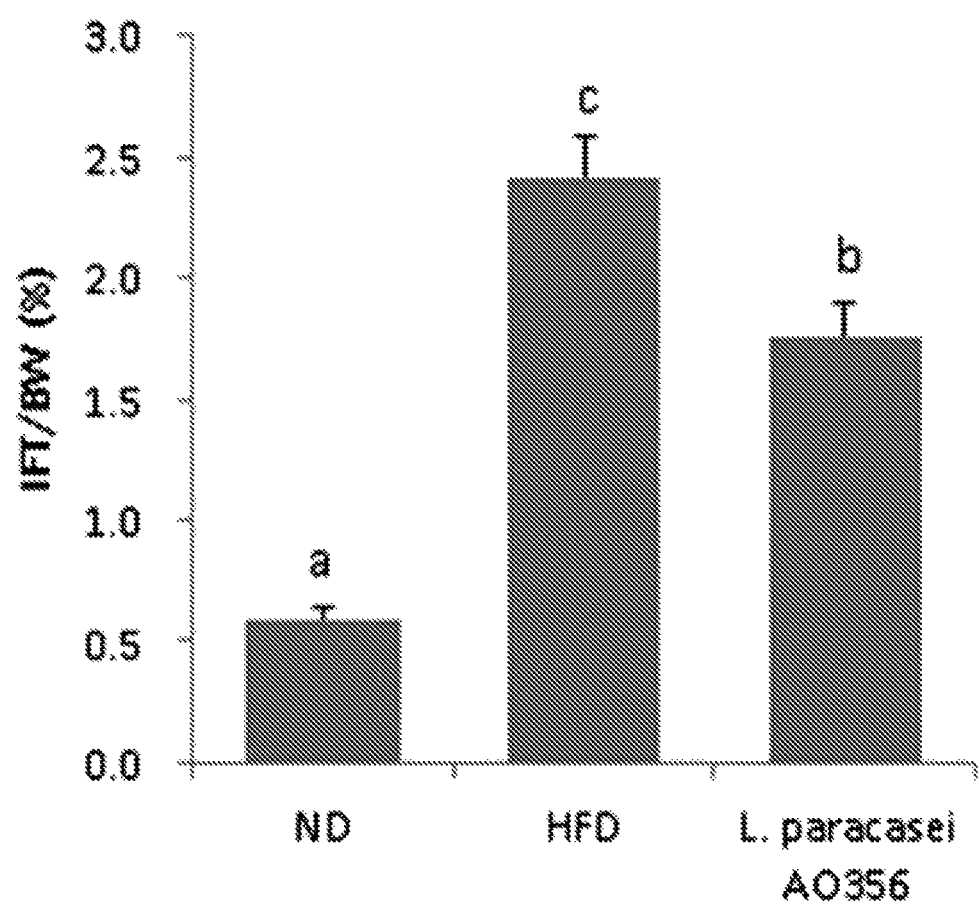
Figure 12E:
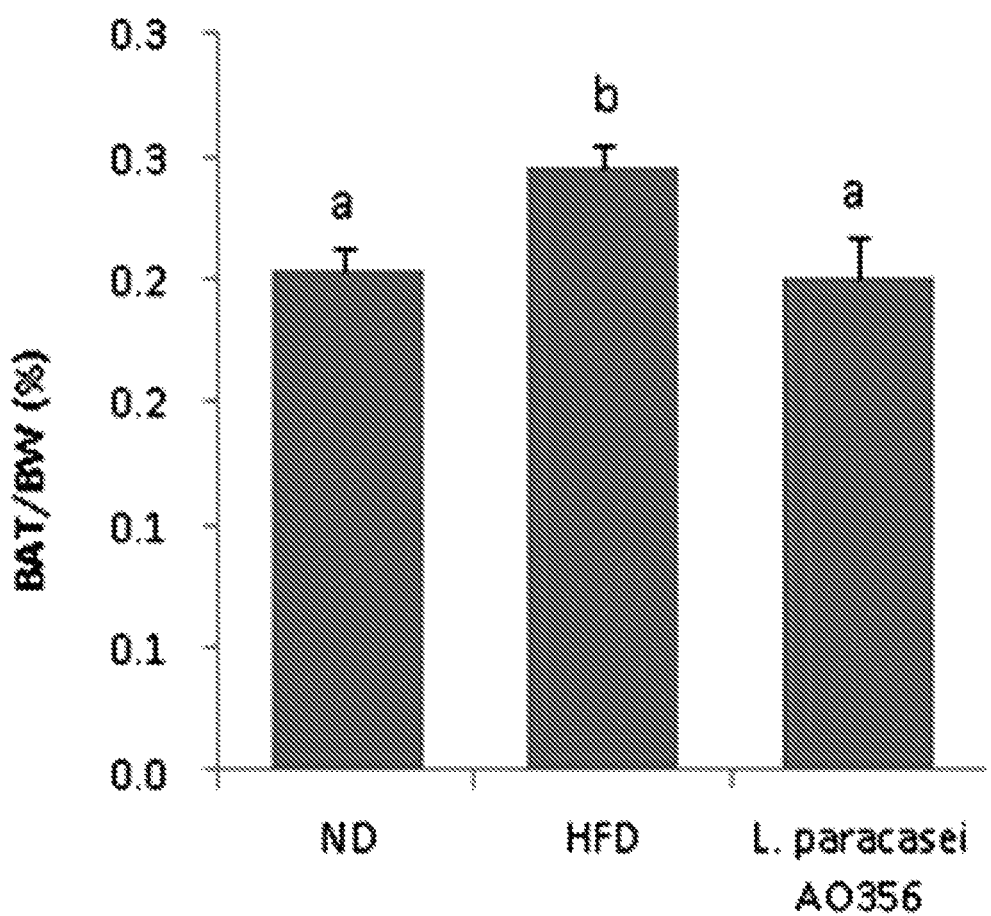
Figure 13A:
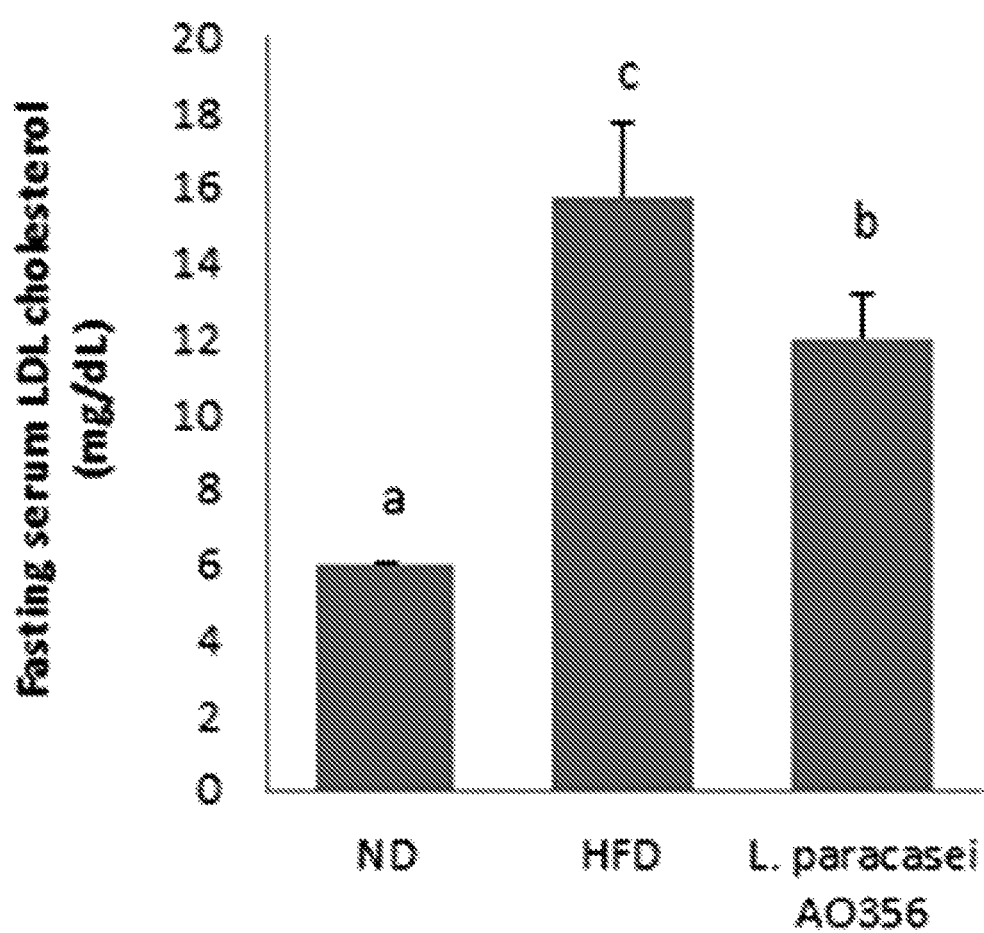
FIGS. 13A-F are a set of graphs showing LDL-cholesterol (A), triglycerides (TG) (B), HDL-cholesterol (C), glucose (D), insulin (E), and HOMA-IR (F), which were measured in serum isolated from each experimental group according to Experimental Example 5 of the present disclosure.
Figure 13B:
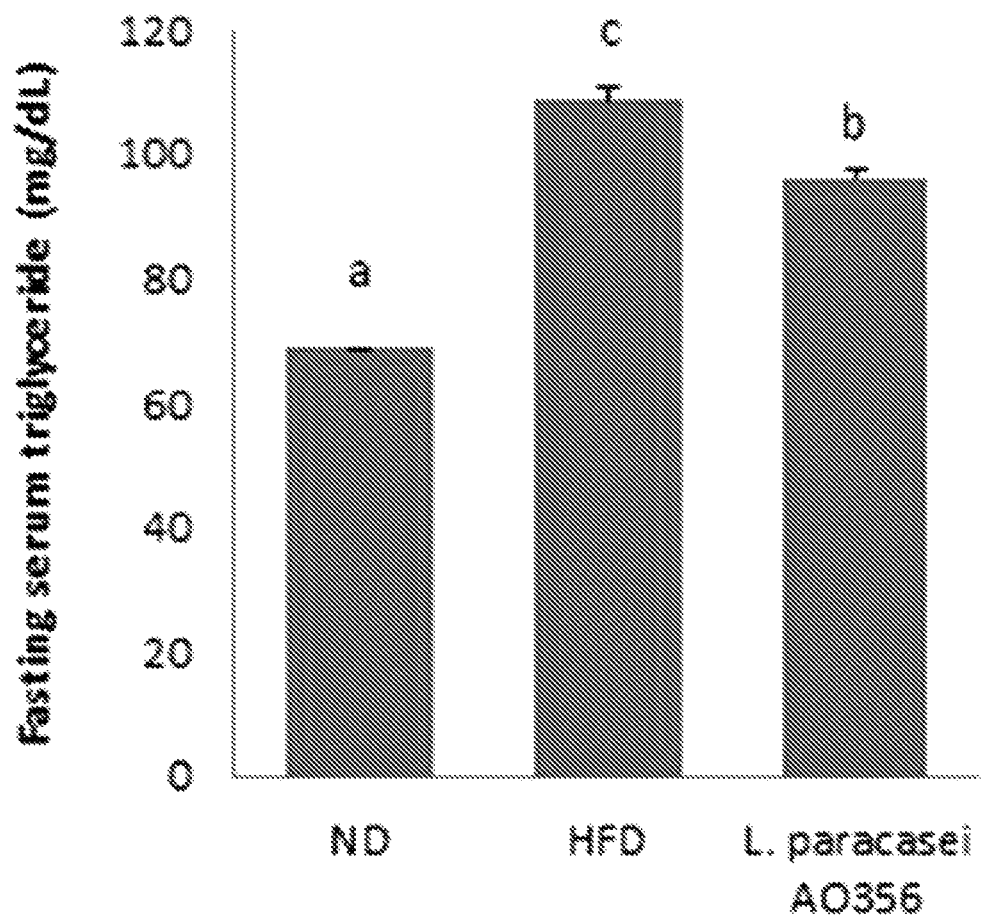
Figure 13C:
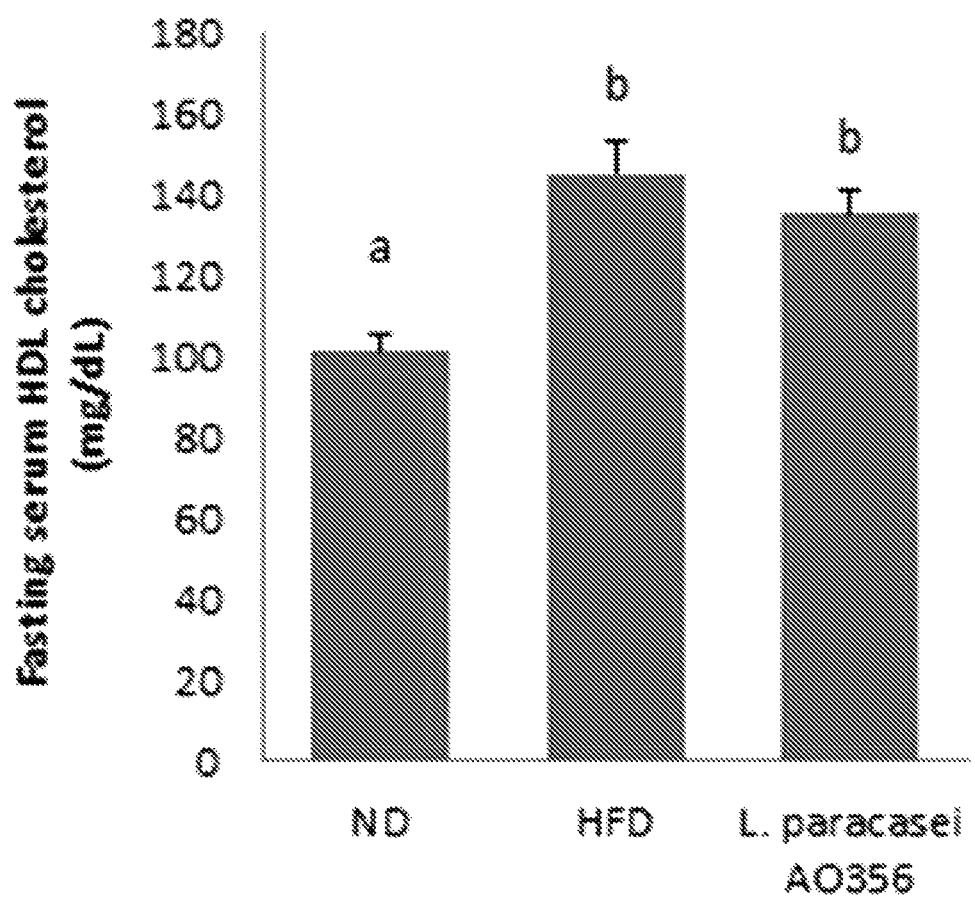
Figure 13D:
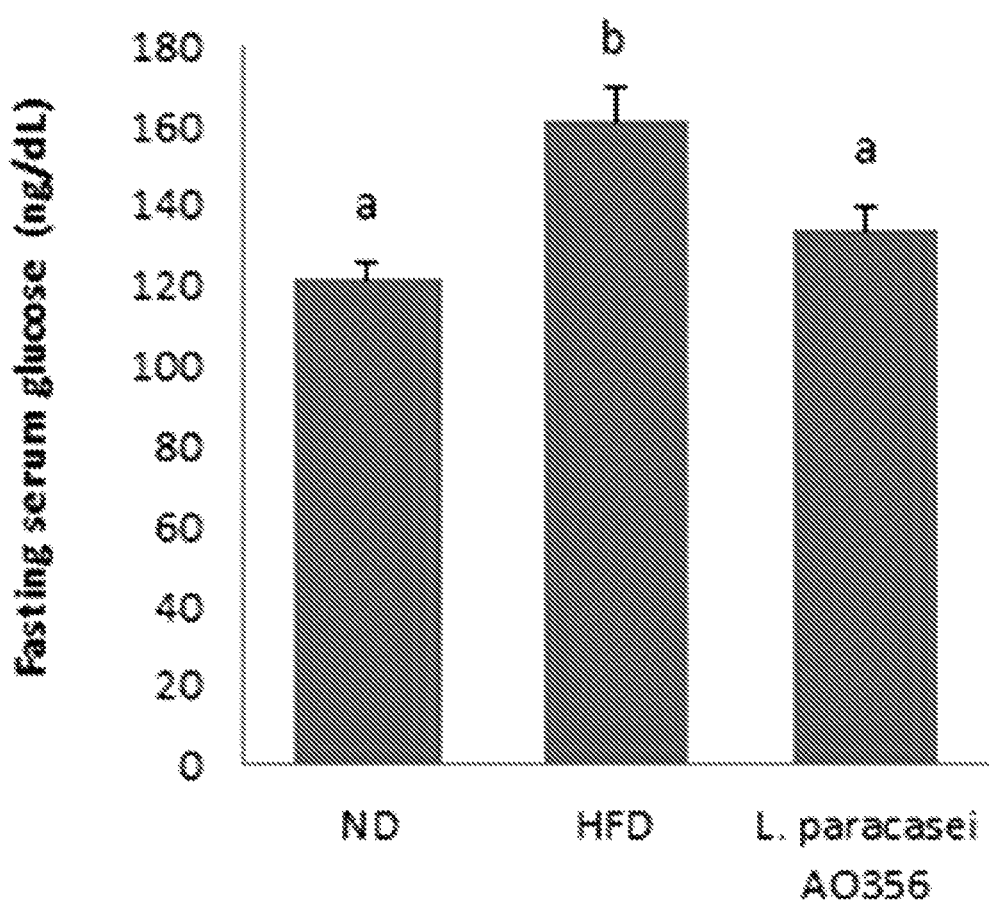
Figure 13E:
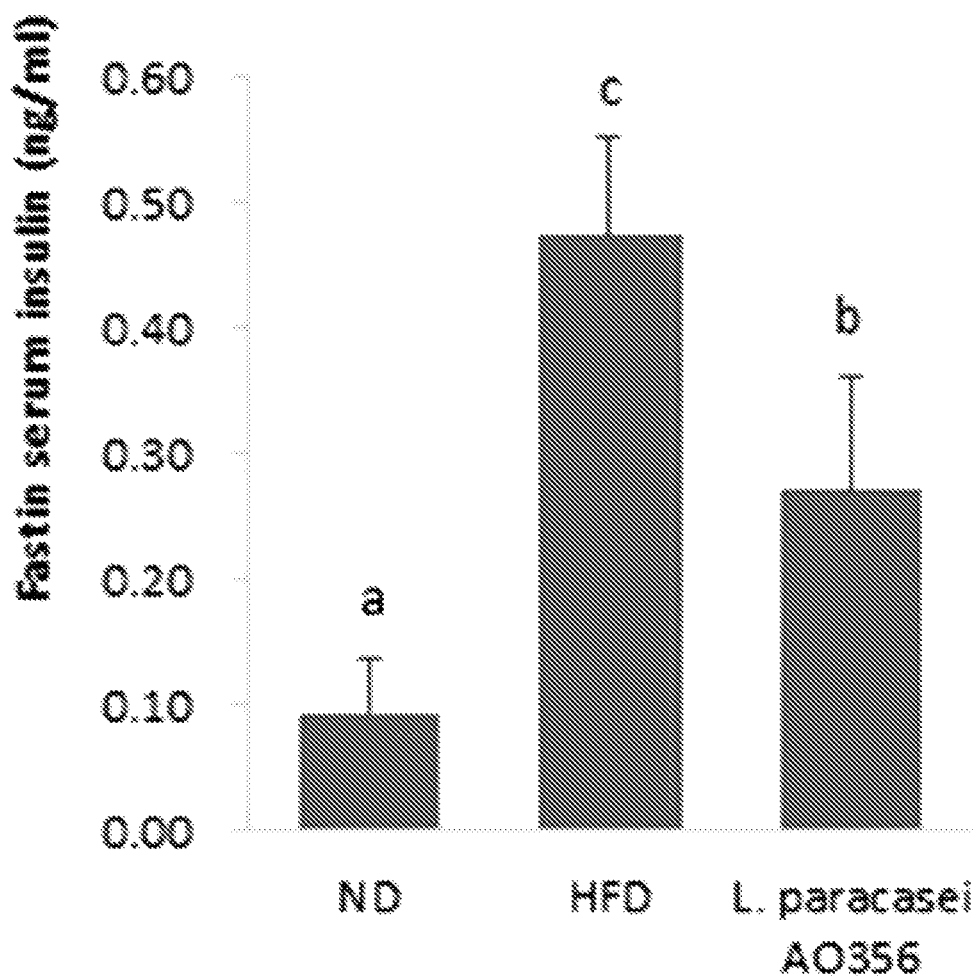
Figure 13F:
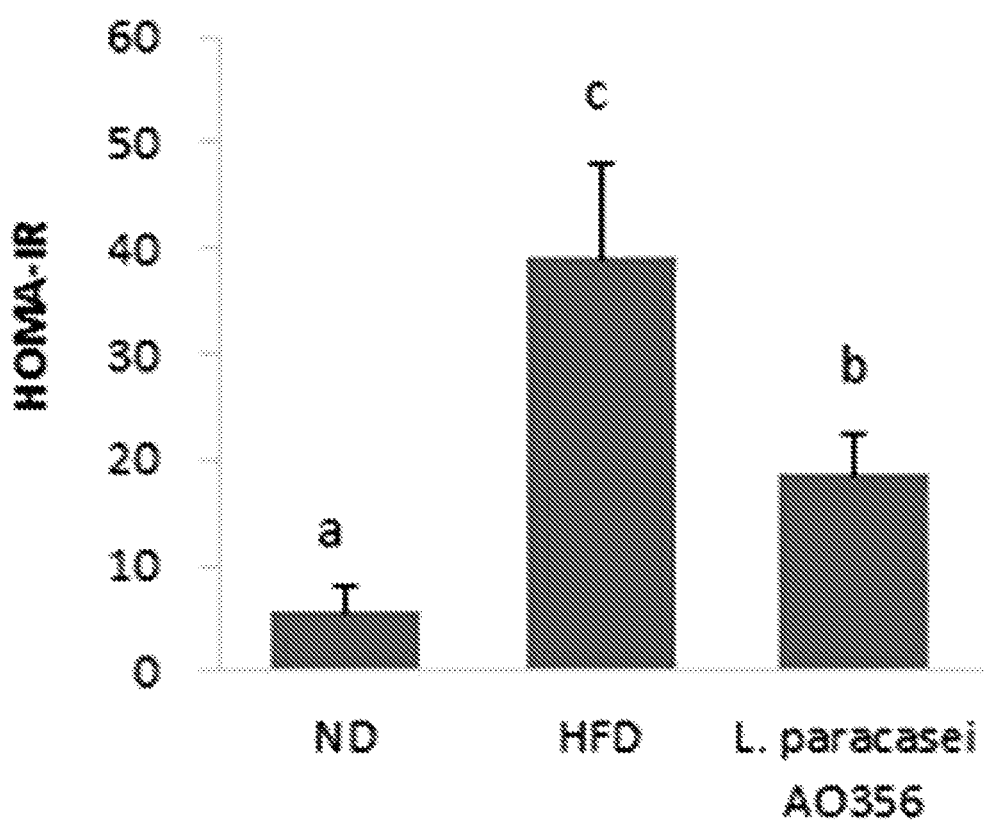

FIG. 10 is a graph showing the results of measuring a body weight change according to week in each experimental group. FIG. 11 is a graph showing the results of analyzing weight gain in each experimental group. The feed intake (g/day), the drinking water intake (g/day), and calorie consumption (kcal/day) are shown in Table 4.

TABLE 4

|  | ND | HFD | *L. paracasei* AO356 | P value |
|---|---|---|---|---|
| Average daily food intake (g/day) | 3.56 ± 0.05 | 2.64 ± 0.04 | 2.55 ± 0.05 | <0.001 |
| Average daily water intake (g/day) | 3.81 ± 0.08 | 2.96 ± 0.09 | 2.99 ± 0.20 | 0.003 |
| Average daily calorie intake (kcal/day) | 12.83 ± 0.17 | 13.36 ± 0.21 | 12.88 ± 0.23 | N.S. |

According to FIGS. 10 and 11 and Table 4, it can be seen that, as a result of administering the *Lactobacillus paracasei* AO356 strain to mice fed high fat feed for 10 weeks, an effect of significantly inhibiting weight gain is shown, compared to the HFD group fed only high fat feed.

That is, since it was confirmed that a body weight that is 10.63% lower than that in the HFD group fed high fat feed was obtained, it was confirmed that, although high fat feed was ingested, the *Lactobacillus paracasei* AO356 strain inhibited weight gain by 31.33% compared to the HFD group, from which it can be seen that the *Lactobacillus paracasei* AO356 strain has an effect of inhibiting weight gain.

The amount of calories consumed was calculated from feed intake. The average daily feed intake and water intake showed significant differences between the ND and HFD groups. This is expected to be due to the difference in the composition and properties of the feed, and it was confirmed that, while the ND group ingested more feed than the HFD group, the water intake also increased.

It is confirmed that the HFD group and *L. paracasei* AO356 group showed no difference in feed intake, water intake, and calorie consumption, from which it can be seen that, the activity of inhibiting weight gain of the *Lactobacillus paracasei* AO356 strain, which was demonstrated through the previous experiments, was not due to a decrease in feed intake or calorie consumption.

D. Analysis of Liver, Epididymal Fat, Retroperitoneal Fat, Inguinal Fat, and Interscapular Fat At the end of the experimental period, the experimental animals were fasted for 12 hours or longer, and then liver tissue, epididymal fat tissue, retroperitoneal fat tissue, inguinal fat tissue, and interscapular brown adipose tissue were extracted and washed with saline to remove moisture, and white fat attached to the interscapular brown adipose tissue was removed. Then, weight in contrast to body weight was measured, and the results thereof are shown in Table 5 below and FIGS. 12A to 12E. In Table 5 and FIGS. 12A to 12E, Liver denotes liver fat, EFT denotes epididymal fat tissue, RFT denotes retroperitoneal fat tissue, IFT denotes inguinal fat tissue, and iBAT denotes interscapular brown adipose tissue.

TABLE 5

| Tissue weight (mg) | ND | HFD | HFD + L. paracasei AO356 | P value |
|---|---|---|---|---|
| Liver | 834.6 ± 15.48 | 916.16 ± 28.37 | 838.88 ± 17.99 | N.S. |
| EFT | 270.49 ± 9.51$^a$ | 1741.68 ± 188.37$^c$ | 1149.36 ± 104.31$^b$ | <0.001 |
| RFT | 82.00 ± 22.96$^a$ | 642.58 ± 57.26$^c$ | 414.01 ± 50.25$^b$ | <0.001 |
| IFT | 159.19 ± 14.20$^a$ | 873.74 ± 84.50$^c$ | 567.89 ± 54.80$^b$ | <0.001 |
| iBAT | 54.27 ± 2.59$^a$ | 88.10 ± 5.91$^c$ | 64.05 ± 5.43$^b$ | 0.001 |
| Serum leptin (pg/ml) | 0.296 ± 0.034$^a$ | 7.200 ± 1.482$^c$ | 3.435 ± 0.756$^b$ | <0.001 |

According to FIGS. 12A-12E and Table 5, it was confirmed that the HFD group fed a high fat diet exhibited a slight increase in the weight of liver tissue compared with the ND group and the *Lactobacillus paracasei* AO356-administered group.

It can also be confirmed that the HFD group fed a high fat diet exhibited great increases in the weights of epididymal fat tissue (EFT), retroperitoneal fat tissue (RFT), inguinal fat tissue (IFT), and interscapular brown adipose tissue (iBAT), whereas, when *Lactobacillus paracasei* AO356 was administered, each tissue exhibited a significant decrease in fat weight.

On the other hand, serum leptin, which is a cytokine secreted from adipose tissue, is known to increase in proportion to an increase in adipose tissue, and is one of the representative indicators of obesity. As a result of examining a change in fat weight, it can be seen that the HFD group fed a high fat diet exhibited an increase in fat weight, whereas, when *Lactobacillus paracasei* AO356 was administered, a significant decrease in fat weight was shown.

E. Serum biochemical analysis

When the experiment was completed, the animal model was fasted for 12 hours or longer, and then blood was collected through retro-orbital blood collection and left at room temperature for 30 minutes or longer, followed by centrifugation at 1,690×g for 10 minutes to separate serum, and the serum was used.

By using the serum, the concentrations of insulin and leptin in the serum were measured using an ELISA-based assay kit. Homeostasis model assessment for insulin resistance (HOMA-IR) was calculated using Equation 1 below by using the measured serum glucose and serum insulin concentrations. Serum triglycerides, HDL-cholesterol and LDL-cholesterol concentrations were measured using colorimetry, and serum glucose concentrations were measured using UV spectrophotometry.

$$\text{HOMA-IR} = \text{fasting glucose (mg/dL)} \times \text{fasting insulin (µU/mL)}/2430 \quad \text{[Equation 1]}$$

FIGS. 13A-13E are a set of graphs showing LDL-cholesterol (a), triglycerides (TG) (b), HDL-cholesterol (c), glucose (d), insulin (e), and HOMA-IR (f), which were measured in serum isolated from each experimental group according to Experimental Example 5 of the present disclosure.

As illustrated in FIGS. 13A-13E, when a high fat diet is repeatedly ingested (HFD group), blood glucose and insulin concentrations are increased, and hyperglycemia and hyperinsulinemia are induced, promoting insulin resistance. This was also confirmed through the experimental examples of the present disclosure.

Specifically, it was confirmed that the HFD group exhibited a significant increase in blood glucose and insulin concentrations compared with the ND group. Furthermore, it was confirmed that, when a *Lactobacillus paracasei* AO356 strain was administered (*L. paracasei* AO356 group), overall decreases in LDL cholesterol, triglycerides (TG), HDL-cholesterol, glucose, and insulin were shown.

It was also confirmed that HOMA-IR, which is calculated using fasting blood glucose and insulin concentrations and is used as an indicator of insulin resistance, was also increased in the HFD group, whereas a significant decrease in HOMA-IR was shown in an *L. paracasei* AO356 group fed the same diet, but administered the *Lactobacillus paracasei* AO356 strain.

Insulin inhibits lipolysis in adipocytes and transports blood fatty acids and glucose into cells to accumulate in the form of triglycerides. As in the HFD group, the action of insulin does not work properly in an insulin-resistant state, resulting in promoted dissociation of fatty acids and decreased activity of lipoprotein lipase (LPL), and consequently, dyslipidemia, in which LDL cholesterol or triglycerides in the blood increase, may occur. That is, it was confirmed that, in the HFD group, dyslipidemia, in which serum triglyceride and LDD cholesterol concentrations increase, occurred, but such a phenomenon could be significantly reduced in the *L. paracasei* AO356 group fed the same high fat diet, but administered the *Lactobacillus paracasei* AO356 strain.

F. RNA Precipitation and qPCR Analysis

The epididymal white fat tissue of each experimental group was partially cut and total RNA was extracted using an RNeasy lipid tissue kit, and cDNA was synthesized using oligo-dT primers. qPCR was performed using a SYBR green qPCR (Qiagen) kit.

Figure 14A:
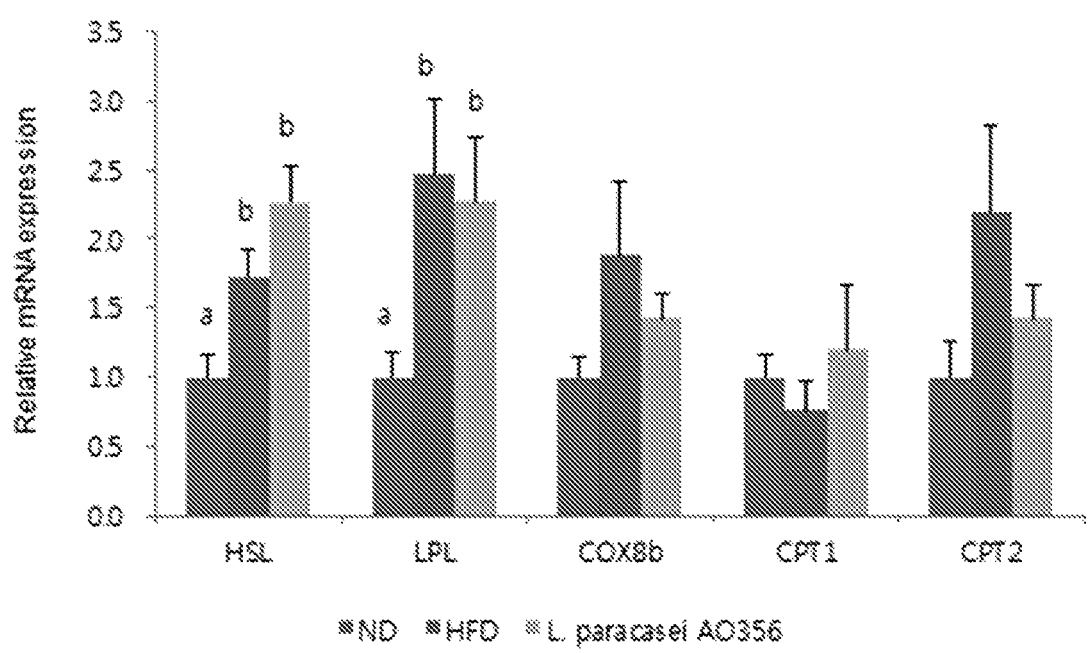
FIGS. 14A-C are a set of graphs showing the results of analyzing the mRNA expression levels of lipometabolism-related genes after extracting RNA from epididymal white fat isolated from each experimental group and performing qPCR analysis thereon, according to Experimental Example 5 of the present disclosure.
Figure 14B:
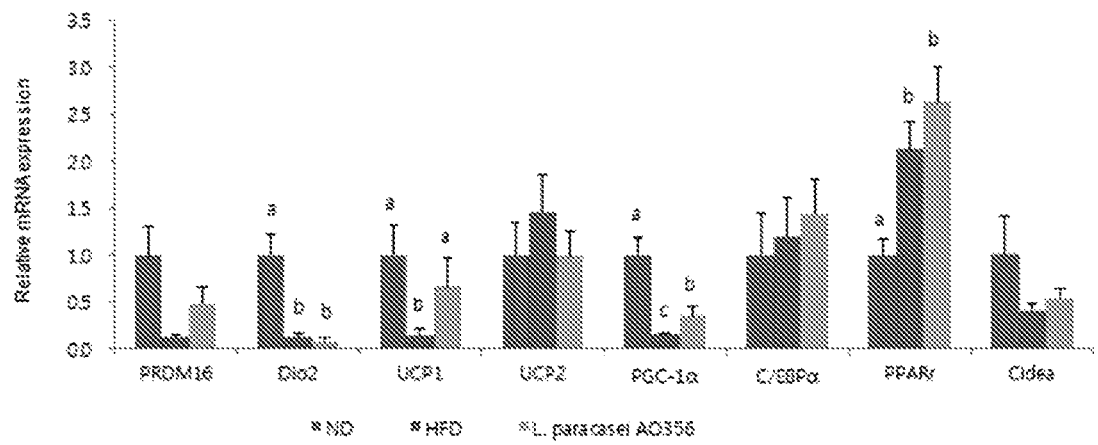
Figure 14C:
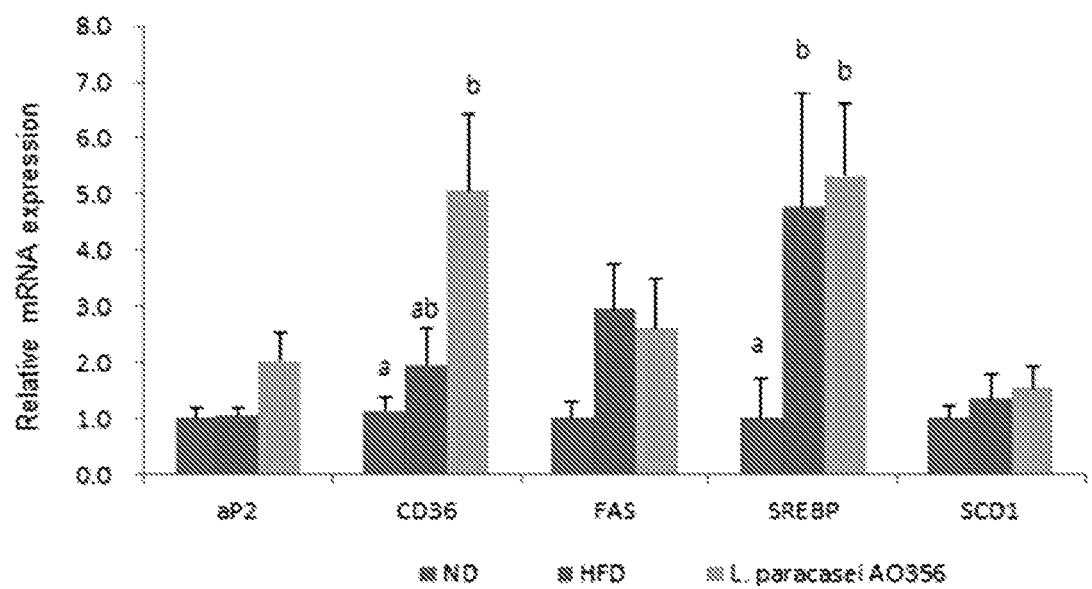

FIGS. 14A-14C are a set of graphs showing the results of analyzing the mRNA expression levels of lipometabolism-related genes after extracting RNA from epididymal white fat tissue isolated from each experimental group and performing qPCR analysis thereon, according to Experimental Example 5 of the present disclosure.

In general, it is known that brown fat among adipose tissues in the body is responsible for energy consumption through heat generation, and white fat is responsible for storing energy in the form of fat. Therefore, in the present disclosure, it was examined whether the *Lactobacillus paracasei* AO356 strain, which was finally selected, coverts white fat into brown fat to thereby have the effect of treating diseases such as obesity.

An increase in the expression rate of UCP1 in white fat promotes the heat generating ability of mitochondria of white fat, the browning/beige fat of white fat is promoted by the increase in the expression rate of the UCP1 gene through a β3-adrenergic agonist, cold exposure, or exercise, and anti-obesity effects through a reduction in body fat, and the like have been reported.

UCP1 plays an important role in the browning of white visceral fat. Referring to FIGS. 14A-14C, it can be confirmed that the expression rate of the UCP1 gene, which had been decreased in the HFD group, was restored in the *L. paracasei* AO356 group.

In addition, PGC1α is a gene that plays an important role in the browning of white fat by promoting the expression rate of the FNDC5 protein that secretes irisin, which is a hormone that promotes the expression of UCP1, and it can be seen that the expression rate of PGC1α was reduced in the HFD group, whereas the expression rate of PGC1α was significantly restored in the *L. paracasei* AO356 group.

In addition, it can be seen that the expression levels of the PRDM16, Cidea, and PPARγ genes were increased via administration of the *Lactobacillus paracasei* AO356 strain, wherein these genes are transcriptional factors that regulate gene programming for browning of white adipose tissue.

Meanwhile, it was confirmed in FIG. 14C that CD36, which had been reduced in the HFD group, was significantly increased by administration of the *Lactobacillus paracasei* AO356 strain, which is necessary for the normal function of brown fat, and particularly, fatty acids play a role in moving polyunsaturated fatty acids into cells, and such polyunsaturated fatty acids act as ligands with the highest affinity, activating PPARγ.

Taken together, it was confirmed that, when the *Lactobacillus paracasei* AO356 strain was administered to an animal model with high fat diet-induced obesity, the strain not only had anti-obesity activity such as a reduction in body fat and inhibition of weight gain by a high fat diet, but also had an effect of increasing the expression of genes related to the browning of white fat.

As is apparent from the foregoing description, a *Lactobacillus paracasei* AO356 strain according to the present disclosure, which is a strain isolated from the human body, has high stability, exhibits the ability to inhibit adipogenic differentiation in vitro and the activity of inducing the differentiation of M1 and M0 macrophages into M2 macrophages, and has excellent activity of alleviating, preventing, or treating obesity, such as the activity of reducing body weight and a reduction in blood lipid concentration through the browning of white fat in animal experiments. Thus, the novel strain of the present disclosure has a low possibility of causing side effects, and therefore, unlike conventional diet functional foods or drugs, which have side effect problems, a diet effect can be exhibited without controlling the dose thereof. Accordingly, the novel strain can be used as a pharmaceutical composition for treating or preventing obesity or a food composition for alleviating or preventing obesity.

Therefore, the novel strain according to the present disclosure can be used as a novel medical substance that is effective in preventing, alleviating, and treating obesity.

It should be understood that embodiments described herein should be considered in a descriptive sense only and not for purposes of limitation.

Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A method of inhibiting weight gain in a mammalian subject in need thereof comprising orally administering to said subject a composition comprising an effective dose of the isolated *Lactobacillus paracasei* AO356 strain that is deposited as KCCM12145P, wherein the *Lactobacillus paracasei* AO356 strain has a 16S rDNA consisting of SEQ ID NO: 1.

2. The method of claim 1, wherein the composition is a pharmaceutical composition comprising $5 \times 10^3$ CFU to $5 \times 10^7$ CFU of the *Lactobacillus paracasei* AO356 strain.

3. The method of claim 1, wherein the *Lactobacillus paracasei* AO356 strain exhibits anti-obesity activity and adipogenesis inhibitory activity.

4. The method of claim 1, wherein the composition is a food composition comprising $5 \times 10^3$ CFU to $5 \times 10^7$ CFU of the *Lactobacillus paracasei* AO356 strain.

5. The method of claim 1, wherein the *Lactobacillus paracasei* AO356 strain is alive or dead.

6. The method of claim 2, wherein the composition comprises a pharmaceutically acceptable carrier.

* * * * *

SEQUENCE LISTING

```
<160> NUMBER OF SEQ ID NOS: 1

<210> SEQ ID NO 1
<211> LENGTH: 1452
<212> TYPE: DNA
<213> ORGANISM: Artificial Sequence
<220> FEATURE:
<223> OTHER INFORMATION: 16s rDNA of Lactobacillus paracasei AO356

<400> SEQUENCE: 1
ggatgaacgc tggcggcgtg cctaatacat gcaagtcgaa cgagttctcg ttgatgatcg      60
gtgcttgcac cgagattcaa catggaacga gtggcggacg ggtgagtaac acgtgggtaa     120
cctgccctta agtgggggat aacatttgga aacagatgct aataccgcat agatccaaga     180
accgcatggt tcttggctga aagatggcgt aagctatcgc ttttggatgg acccgcggcg     240
tattagctag ttggtgaggt aatggctcac caaggcgatg atacgtagcc gaactgagag     300
gttgatcggc cacattggga ctgagacacg gcccaaactc ctacgggagg cagcagtagg     360
```

```
gaatcttcca caatggacgc aagtctgatg gagcaacgcc gcgtgagtga agaaggcttt       420
cgggtcgtaa aactctgttg ttggagaaga atggtcggca gagtaactgt tgtcggcgtg       480
acggtatcca accagaaagc cacggctaac tacgtgccag cagccgcggt aatacgtagg       540
tggcaagcgt tatccggatt tattgggcgt aaagcgagcg caggcggttt tttaagtctg       600
atgtgaaagc cctcggctta accgaggaag cgcatcggaa actgggaaac ttgagtgcag       660
aagaggacag tggaactcca tgtgtagcgg tgaaatgcgt agatatatgg aagaacacca       720
gtggcgaagg cggctgtctg gtctgtaact gacgctgagg ctcgaaagca tgggtagcga       780
acaggattag ataccctggt agtccatgcc gtaaacgatg aatgctaggt gttggagggt       840
ttccgccctt cagtgccgca gctaacgcat taagcattcc gcctggggag tacgaccgca       900
aggttgaaac tcaaaggaat tgacgggggc ccgcacaagc ggtggagcat gtggtttaat       960
tcgaagcaac gcgaagaacc ttaccaggtc ttgacatctt ttgatcacct gagagatcag      1020
gtttcccctt cggggggcaaa atgacaggtg gtgcatggtt gtcgtcagct cgtgtcgtga      1080
gatgttgggt taagtcccgc aacgagcgca acccttatga ctagttgcca gcatttagtt      1140
gggcactcta gtaagactgc cggtgacaaa ccggaggaag gtggggatga cgtcaaatca      1200
tcatgcccct tatgacctgg gctacacacg tgctacaatg gatggtacaa cgagttgcga      1260
gaccgcgagg tcaagctaat ctcttaaagc cattctcagt tcggactgta ggctgcaact      1320
cgcctacacg aagtcggaat cgctagtaat cgcggatcag cacgccgcgg tgaatacgtt      1380
cccgggcctt gtacacaccg cccgtcacac catgagagtt tgtaacaccc gaagccggtg      1440
gcgtaaccct tt                                                         1452
```